(12) United States Patent
Parce et al.

(10) Patent No.: US 6,649,358 B1
(45) Date of Patent: Nov. 18, 2003

(54) MICROSCALE ASSAYS AND MICROFLUIDIC DEVICES FOR TRANSPORTER, GRADIENT INDUCED, AND BINDING ACTIVITIES

(75) Inventors: J. Wallace Parce, Palo Alto, CA (US); C. Nicholas Hodge, Los Altos Hills, CA (US); H. Garrett Wada, Atherton, CA (US)

(73) Assignee: Caliper Technologies Corp., Hopkinton, MA (US)

( * ) Notice: Subject to any disclaimer, the term of this patent is extended or adjusted under 35 U.S.C. 154(b) by 0 days.

(21) Appl. No.: 09/579,111

(22) Filed: May 25, 2000

Related U.S. Application Data
(60) Provisional application No. 60/191,784, filed on Mar. 24, 2000, provisional application No. 60/176,093, filed on Jan. 14, 2000, provisional application No. 60/176,001, filed on Jan. 12, 2000, and provisional application No. 60/155,259, filed on Jun. 1, 1999.

(51) Int. Cl.[7] .................. G01N 33/567; C12Q 1/00
(52) U.S. Cl. .............. 435/7.2; 435/7.93; 435/287.3; 435/288.5; 435/4; 435/7.1; 436/538
(58) Field of Search ............. 435/4, 7.1, 7.2, 435/7.92, 7.93, 7.94, 5, 287.1, 287.2, 287.3, 288.5; 436/514, 538; 422/61

(56) References Cited

U.S. PATENT DOCUMENTS

| | | | |
|---|---|---|---|
| 4,390,403 A | | 6/1983 | Batchelder |
| 4,444,879 A | * | 4/1984 | Foster et al. .............. 422/56 |
| 4,908,112 A | | 3/1990 | Pace |
| 5,010,175 A | | 4/1991 | Rutter et al. |
| 5,126,022 A | | 6/1992 | Soane et al. |
| 5,271,724 A | | 12/1993 | van Lintel |
| 5,277,556 A | | 1/1994 | van Lintel |
| 5,288,514 A | | 2/1994 | Ellman |
| 5,375,979 A | | 12/1994 | Trah |
| 5,498,392 A | | 3/1996 | Wilding et al. |

(List continued on next page.)

FOREIGN PATENT DOCUMENTS

| | | |
|---|---|---|
| WO | WO 91/19735 | 12/1991 |
| WO | WO 92/00091 | 1/1992 |
| WO | WO 94/05414 | 3/1994 |
| WO | WO 96/04547 | 2/1996 |
| WO | WO 97/02357 | 1/1997 |
| WO | WO 98/00231 | 1/1998 |
| WO | WO 98/00705 | 1/1998 |
| WO | WO 98/00707 | 1/1998 |

(List continued on next page.)

OTHER PUBLICATIONS

Ager, A. (1994) "Lymphocyte Recirculation and Homing: Roles of Adhesion Molecules and Chemoattractants" *Trends Cell Biol.* 4:326–333.

Bargatze, R.F. et al. (1995) "Distinct Roles of L–Selectin and Integrins α4β7 and LFA–1in Lymphocyte Homing to Peyer's Patch–HEV In Situ: The Multistep Model Confirmed and Refined" *Immunity* 3:99–108.

Bradley, L.M. and Watson, S.R. (1996) "Lymphocyte Migration Into Tissue: The Paradigm Derived From CD4 Subsets" *Curr. Opin. Immunol.* 8:312–320.

Campbell et al., J. Org. Chem. 59:658–60 (1994).

Chen et al., J. Amer. Chem. Soc. 116:2661–62 (1994).

Cho et al., Science 261:1303–05 (1993).

Dianzani, U. and Malavasi, F. (1995) "Lymphocyte Adhesion to Endothelium" *Crit. Rev. Immunol.* 15:167–199.

Furka, Int. J. Pept. Prot. Res. 37:487–493 (1991).

(List continued on next page.)

*Primary Examiner*—Padmashri Ponnaluri
*Assistant Examiner*—My Chau T Tran
(74) *Attorney, Agent, or Firm*—Donald R. McKenna; Quine Intellectual Property Law Group

(57) ABSTRACT

Methods of monitoring transporter activity, gradient induced activity, and binding activity in microscale systems, as well as corresponding microscale devices, systems and kits are provided.

19 Claims, 10 Drawing Sheets

U.S. PATENT DOCUMENTS

| | | | |
|---|---|---|---|
| 5,506,337 A | | 4/1996 | Summerton et al. |
| 5,519,134 A | | 5/1996 | Acevedo et al. |
| 5,525,735 A | | 6/1996 | Gallop et al. |
| 5,536,382 A | * | 7/1996 | Sunzeri ................. 422/56 |
| 5,539,083 A | | 7/1996 | Cook et al. |
| 5,549,974 A | | 8/1996 | Holmes |
| 5,569,588 A | | 10/1996 | Ashby et al. |
| 5,571,398 A | | 11/1996 | Karger et al. |
| 5,571,410 A | | 11/1996 | Swedberg et al. |
| 5,585,069 A | | 12/1996 | Zanzucchi et al. |
| 5,587,128 A | | 12/1996 | Wilding et al. |
| 5,593,838 A | | 1/1997 | Zanzucchi et al. |
| 5,593,853 A | | 1/1997 | Chen et al. |
| 5,603,351 A | | 2/1997 | Cherukuri et al. |
| 5,635,358 A | | 6/1997 | Wilding et al. |
| 5,637,469 A | | 6/1997 | Wilding et al. |
| 5,699,157 A | | 12/1997 | Parce |
| 5,716,852 A | | 2/1998 | Yager et al. |
| 5,750,015 A | | 5/1998 | Soane et al. |
| 5,766,848 A | * | 6/1998 | Borden et al. ............. 435/7.2 |
| 5,779,868 A | | 7/1998 | Parce et al. |
| 5,800,690 A | | 9/1998 | Chow et al. |
| 5,842,787 A | | 12/1998 | Kopf-Sill et al. |
| 5,852,495 A | | 12/1998 | Parce |
| 5,858,195 A | | 1/1999 | Ramsey |
| 5,869,004 A | | 2/1999 | Parce et al. |
| 5,872,010 A | | 2/1999 | Karger et al. |
| 5,876,675 A | | 3/1999 | Kennedy |
| 5,880,071 A | | 3/1999 | Parce et al. |
| 5,882,465 A | | 3/1999 | McReynolds |
| 5,885,470 A | | 3/1999 | Parce et al. |
| 5,942,443 A | | 8/1999 | Parce et al. |
| 5,948,227 A | | 9/1999 | Dubrow |
| 5,955,028 A | | 9/1999 | Chow |
| 5,957,579 A | | 9/1999 | Kopf-Sill et al. |
| 5,958,203 A | | 9/1999 | Parce et al. |
| 5,958,694 A | | 9/1999 | Nikiforov |
| 5,959,291 A | | 9/1999 | Jensen |
| 5,964,995 A | | 10/1999 | Nikiforov et al. |
| 5,965,001 A | | 10/1999 | Chow et al. |
| 5,965,410 A | | 10/1999 | Chow et al. |
| 5,972,187 A | | 10/1999 | Parce et al. |
| 5,976,336 A | | 11/1999 | Dubrow et al. |
| 5,989,402 A | | 11/1999 | Chow et al. |
| 6,001,231 A | | 12/1999 | Kopf-Sill |
| 6,004,515 A | | 12/1999 | Parce et al. |
| 6,011,252 A | | 1/2000 | Jensen |
| 6,012,902 A | | 1/2000 | Parce |
| 6,042,710 A | | 3/2000 | Dubrow |
| 6,046,056 A | | 4/2000 | Parce et al. |
| 6,068,752 A | | 5/2000 | Dubrow et al. |
| 6,071,478 A | | 6/2000 | Chow |
| 6,074,725 A | | 6/2000 | Kennedy |
| 6,080,295 A | | 6/2000 | Parce et al. |
| 6,103,199 A | * | 8/2000 | Bjornson et al. ........ 435/288.4 |
| 6,103,537 A | * | 8/2000 | Ullman et al. ........... 422/82.01 |
| 6,274,337 B1 | * | 8/2001 | Parce et al. ............. 435/287.1 |

FOREIGN PATENT DOCUMENTS

| | | |
|---|---|---|
| WO | WO 98/02728 | 1/1998 |
| WO | WO 98/05424 | 2/1998 |
| WO | WO 98/22811 | 5/1998 |
| WO | WO 98/45481 | 10/1998 |
| WO | WO 98/45929 | 10/1998 |
| WO | WO 98/46438 | 10/1998 |
| WO | WO 98/49548 | 11/1998 |
| WO | WO 98/55852 | 12/1998 |
| WO | WO 98/56505 | 12/1998 |
| WO | WO 98/56956 | 12/1998 |
| WO | WO 99/00649 | 1/1999 |
| WO | WO 99/43432 | 2/1999 |
| WO | WO 99/10735 | 3/1999 |
| WO | WO 99/12016 | 3/1999 |
| WO | WO 99/16162 | 4/1999 |
| WO | WO-9917119 | 4/1999 |
| WO | WO 99/19056 | 4/1999 |
| WO | WO 99/19516 | 4/1999 |
| WO | WO 99/29497 | 6/1999 |
| WO | WO 99/31495 | 6/1999 |
| WO | WO 99/34205 | 7/1999 |
| WO | WO 99/44217 | 9/1999 |
| WO | WO 93/20242 | 10/1999 |
| WO | WO 99/56954 | 11/1999 |
| WO | WO 00/09753 | 2/2000 |

OTHER PUBLICATIONS

Grey, H. et al. (1989) "How T Cells See Antigen" *Sci.Am.* 261(5):56–64.

Hagihara et al., J. Amer. Chem. Soc. 114:6568–70 (1992).

Hirschmann et al., J. Amer. Chem. Soc. 114:9217–9218 (1992).

Hobbs et al., Proc. Nat. Acad. Sci. USA 90:6909–6913 (1993).

Hogg, N. and Berlin, C. (1995) "Structure and Function of Adhesion Receptors in Leukocyte Trafficking" *Immunol. Today* 16 pp. 327–330.

Houghton et al., Nature 354:84–88 (1991).

Hynes, R.O. (1992) "Contact and Adhesive Specificities in the Associations, Migrations, and Targeting of Cells and Axons" *Cell* 16:303–321.

Hynes, R.O. (1994) "The Impact of Molecular Biology on Models for Cell Adhesion" *Bioessays* 16:663–669.

Liang et al., Science, 274:1520–1522 (1996).

Vaughn et al., Nature Biotechnology, 14(3):309–314 (1996).

Ramsey, J.M. et al., "Microfabricated chemical measurement systems," *Nature Med.* (1995) 1:1093–1096.

Seiler, K. et al., "Planar Glass Chips for Capillary Electrophoresis: Repetitive Sample Injection, Quantitation, and Separation Efficiency," *Anal. Chem.* (1993) 65:1481–1488.

Seiler, K. et al., "Electroosmotic Pumping and Valveless Control of Fluid Flow Within a Manifold of Capillaries on a Glass Chip," *Anal. Chem.* (1994) 66:3485–3491.

Sundberg, S. A., "High–throughput and ultra–high–throughput screening: solution—and cell–based approches," *Current Opinions in Biotechnology* 2000, 11:47–53.

Cohen, C.B. et al., "A Microchip–Based Enzyme Assay for Protein Kinase A," *Anal. Chem.* (1999) 273:89–97.

Dasgupta, P.K. et al., "Electroosmosis: A Reliable Fluid Propulsion System for Flow InJection Analysis," *Anal. Chem.* (1994) 66:1792–1798.

Jacobson, S.C. et al., "Fused Quartz Substrates for Microchip Electrophoresis," *Anal. Chem.* (1995) 67:2059–2063.

Manz, A. et al., "Electroosmotic pumping and electrophoretic separations for miniaturized chemical analysis systems," *J. Micromech. Microeng.* (1994) 4:257–265.

Knight, J.B. et al., "Hydrodynamic Focusing on a Silicon Chip: Mixing Nanoliters in Microseconds" *Phys. Rev. Letts.* (1998) 80(17):3863–3866.

Kugelmass, S.M. et al., "Fabrication and Characterization of Three–Dimensional Microfluidic Arrays" *Proc. Of SPIE* (1999) 3877:88–94.

* cited by examiner

MICROSCALE ASSAYS AND MICROFLUIDIC DEVICES FOR TRANSPORTER, GRADIENT INDUCED, AND BINDING ACTIVITIES

CROSS-REFERENCES TO RELATED APPLICATIONS

This application is related to Ser. No. 09/323,747, filed on Jun. 1, 1999 (converted to Provisional U.S. Patent Application No. 60/155,259, to J. Wallace Parce, et al., and entitled "Microscale Assay and Microfluidic Device for Transporter Activity") and to Provisional U.S. Patent Application No. 60/176,001, filed Jan. 12, 2000; No. 60/176,093, filed Jan. 14, 2000; and No. 60/191,784, filed Mar. 24, 2000, each to J. Wallace Parce, et al. and each entitled "Microscale Assays and Microfluidic Devices for Transporter, Gradient Induced, and Binding Activities." The present application claims priority to and the benefit of each of these earlier applications, pursuant to 35 U.S.C. §119(e), as well as any other applicable statute or rule. These prior applications are incorporated herein in their entirety for all purposes.

BACKGROUND OF THE INVENTION

Model systems which mimic receptor binding and other cell-based assays are of increasing importance in molecular biology. Phenomena such as transporter activity, pre- and post-synaptic cell interactions, chemotactic response, enzyme-ligand binding and the like are of relevance to pharmacology, clinical chemistry and basic research.

For example, one clinically relevant system involves the interaction of cells at synapses. At least two general types of synapses exist in nature. In electrical synapses, gap junctions connect cells which are in communication. Gap junctions permit direct transmission of electrical impulses from a presynaptic cell to a postsynaptic cell.

In the more common chemical synapse, an axon terminal of a presynaptic cell contains vesicles filled with a neurotransmitter, such as epinephrine or acetylcholine, which is released by exocytosis when a nerve impulse reaches the axon terminal. The vesicles release their contents into the synaptic cleft and the transmitter diffuses across the synaptic cleft. After a brief lag time (e.g., about 0.5 ms) the transmitter binds to receptors on postsynaptic cells. This typically causes a change in ion permeability and electrical potential in the postsynaptic cell. Excitatory signals induce an action potential in the postsynaptic neuron. Inhibitory signals prevent production of an action potential in the postsynaptic neuron. Both inhibitory and excitatory signals can exist simultaneously in the same synaptic cleft, depending on the cell types, neurotransmitters, etc. Similarly, a postsynaptic cell can be in simultaneous contact with multiple presynaptic cells, each of which can transmit both excitatory and inhibitory signals to the postsynaptic cell.

The presence of transmitter in the synapse is regulated in a variety of ways, thereby controlling the signal received by the postsynaptic cell. For example, some cells and vesicles actively transport transmitter out of the synapse, thereby reducing the presence of the transmitter in the junction. Similarly, oxidases and other enzymes degrade some neurotransmitters in the synapse. Neurotransmitters can also diffuse away from the synapse. For a review of neurotransmitter and transporter systems, see, *Neurotransmitter Transporters: Structure, Function and Regulation* (1997) M. E. A. Reith, ed. Human Press, Towata N.J., and the references cited therein.

Transporters have a variety of important biological roles. For example, the $Na^+/Cl^-$ dependent transporters (e.g., the monoamine transporters, as well as betaine, creatine, GABA, glycine, proline and taurine carriers) are the primary sites of action for a variety of drugs of both therapeutic and abuse potential. For example, among the monoamine transporters, inhibition of the dopamine transporter (DAT) is linked to euphoric and reinforcing properties of psychomotor stimulants such as cocaine and amphetamines. The major classes of therapeutic antidepressants act by inhibiting the norepinephrine and serotonin transporters (NET and SERT) and many of these compounds have proved clinically useful in the treatment of panic, stress, obsessive compulsive disorders, and other conditions.

Chemotactic responses have also long been known to play significant roles in various biologicial systems. Chemotaxis is the capacity of a motile cell to respond to chemical changes in its environment by directed movement. The migration of a motile cell exhibiting a chemotactic response can be either up or down a concentration gradient of a chemotactic factor. For example, phagocytic cells like macrophages are attracted by and move toward various substances generated in an immune response, whereas other motile cells including certain bacteria can move either toward an attractant (e.g., assorted sugars) or away from various repellents (e.g., phenol). For further discussion of chemotaxis and related components, including adhesion and chemotactic factors, see, Kuby, *Immunology*, $3^{rd}$ Ed. W. H. Freeman and Company, New York (1997) and Stryer, *Biochemistry*, $4^{th}$ Ed., W. H. Freeman and Company, New York (1995).

Aside from methods and devices for modeling transporter activity and chemotactic responses, general binding assays for studying, e.g., enzyme-ligand binding interactions, receptor-ligand binding interactions, and the like are also useful, e.g., in modeling biological systems.

In general, existing in vitro systems for studying transmitters, transporters, presynaptic and postsynaptic cells, and other aspects of cell signaling do not provide ideal high-throughput methods and devices for modeling and mimicking transmitter diffusion, transporter activity, transmitter activity, and the like. More generally, cell-cell signaling, which is central to biological activity, is not ideally modeled using existing technologies and additional high throughput methods of screening for modulators of signaling activities are desirable. Furthermore, progress in the study of chemotaxis and various binding activities has also been impeded by in vitro assays that are tedious to perform and whose results have been difficult to quantify. As such, automated and quantitative assays for all of these important biological processes are desirable.

The present invention provides these and other features by providing high-throughput microscale systems for modeling transporter activity, transmitter degradation activity, transmitter activity, cell signaling, and detection of modulators (inhibitors and enhancers) of transporter or transmitter degradation activity. The present invention also relates to high-throughput systems for modeling gradient induced activities, e.g., chemotactic responses, and for assessing general binding activities. These and many other features which will be apparent upon complete review of the following disclosure.

SUMMARY OF THE INVENTION

The invention provides methods, devices, kits, reagents and related materials for modeling various important biological processes. For example, the present invention is optionally used to determine the activity of transporter components such as neurotransmitter transporters (for example, the neurotransmitter acetylcholine is specifically internalized by cells via endocytosis of acetylcholine from the synaptic cleft during the recovery period following signal transmission). The invention is also optionally used to assess gradient induced activities (e.g., study chemotactic responses) and to evaluate the binding activity of, e.g., various biological components. The methods are typically conducted in a microscale format using a microfluidic system which includes or is coupled to sources of the relevant assay components.

In the transporter-related methods and assays of the invention, a first component which includes transporter activity is flowed through a first channel. A second component which produces a detectable signal upon exposure to a transportable molecule or set of transportable molecules is flowed into the first channel. The transportable molecule is flowed into the first channel and a signal produced by contacting the second component with the transportable molecule is then detected. Typically, the level of signal product is inversely related to transporter activity.

A variety of formats for the methods are appropriate. The first and second components are typically flowed sequentially (a typical configuration) or simultaneously in the first channel. The second component optionally is flowed into contact with the transportable molecule in the presence or absence of the first component (for example, if flowed in the absence of the first component, the resulting signal serves as a positive control for the signal produced by contacting the second component with the transportable molecule).

Known activity modulators are optionally incorporated into assay schemes as controls for modulation of a particular transporter. For example, paraxetine, citalopram, fluxetine, imipramine, amitriptyline, mazindol, cocaine, desipramine, nomifensine, GBR12909, D-amphetamine, L-amphetamine, nortriptyline, DA, MPP$^+$, NE, and 5-HT are known inhibitors of the transport of human monoamine clones. See, *Neurotransmitter Transporters: Structure, Function and Regulation,* e.g., at chapter 1 (1997) M. E. A. Reith, ed. Human Press, Towata N.J., and the references cited therein.

The first component is typically a cell or component with similarity to a cell such as a cell membrane (or other lipid membrane preparation) having transporter activity. Similarly, the second component is typically, e.g., a cell, cell membrane (or other lipid membrane preparation), or other biological or synthetic moiety comprising a receptor for the transportable molecule which is capable of producing a detectable signal upon exposure to a transportable molecule (e.g., a transmitter). The first or second components typically include a transporter or transmitter receptor carrier moiety or set of carrier moieties which includes a receptor or transporter. A "carrier" is a component comprising the specified activity (e.g., transporter, transmitter, transmitter receptor, etc.). Examples of carriers or carrier sets include cells, liposomes, organelles, proteins, and protein-lipid complexes. Examples of transportable molecules or set of transportable molecules include proteins, sets of proteins, peptides, sets of peptides, lipids, sets of lipids, carbohydrates, sets of carbohydrates, organic molecules, sets of organic molecules, drugs, sets of drugs, receptor ligands, sets of receptor ligands, antibodies, sets of antibodies, neurotransmitters, sets of neurotransmitters, cytokines, sets of cytokines, chemokines, sets of chemokines, hormones, sets of hormones and a variety of other biologically active and inactive molecules. In preferred aspects, the first component is a carrier moiety or set of carrier moieties comprising a transporter activity having neurotransporter activity.

Preferred transporter components include cells which specifically or non-specifically internalize transmitter molecules, e.g., by specific or non-specific endocytosis, or pinocytosis. These transporter molecules, such as the Na$^+$/Cl$^-$ dependent transporters (e.g., the monoamine transporters, as well as betaine, creatine, GABA, glycine, proline and taurine carriers), transport corresponding transportable molecules such as acetylcholine, catecholamines (e.g., epinephrine, norepinephrine, dopamine, serotonin, and other adrenergic neurotransmitters), endorphins (e.g., α and β-endorphin), enkephalins (e.g., Met-enkephalin or Leu-enkephalin), somatostatin, leutinizing hormone-releasing hormone, thyrotropin-releasing hormone, substance P, angiotensin I, angiotensin II, vasoactive intestinal peptide, serotonin, and gamma-aminobutyric acid (GABA).

In one aspect of the invention, the transportable molecule is flowed from a second channel into the first channel and the second component is flowed from a third channel into the first channel, where the first component, the second component and the transportable molecule mix. For example, the second and third channels optionally intersect the first channel in a mixing region, where the first, second and third components diffuse into contact in the mixing region. An advantage to this arrangement is that the diffusion mimics diffusion of components in synapses in vivo, providing a convenient way of modeling transport of biologically active transportable molecules such as neurotransmitters. The first and second components are optionally flowed sequentially, serially or concomitantly. Potential transport modulatory compounds (e.g., inhibitors) are optionally flowed into contact with the first component to test for an effect on transport of the transportable molecule. For example, the modulatory compound is optionally flowed into the first channel prior to introduction of the second component and the transportable molecule, or concomitant with flow of the transportable molecule, depending on the format of the particular assay.

In one embodiment, concentration of the transportable molecule is decreased in solution in the first channel as the first component internalizes the transportable molecule. In other aspects, the first component sequesters or otherwise inactivates the transportable molecule.

A detectable signal produced by transport of the transportable molecule, or inhibition of transport of the transportable molecule provides an indication of, e.g., the transporter activity present in the first component, or an ability of the inhibitor to inhibit the transporter activity present in the first component, or an ability of the second component to sequester the transportable molecule. For example, the detectable signal is optionally a cellular activity, a light emission, a radioactive emission, a change in pH, a change in temperature, or the like. The concentration of the first component, the transportable molecule, or the second component (or any combination of these components), as well as potential modulators is optionally varied in the first channel and the resulting increase or decrease in signal strength is typically measured.

The present invention also relates to methods of detecting a gradient induced activity. The methods include providing a first channel, e.g., a microchannel, with an internal surface including a first and a second longitudinal segment. A first component (e.g., an adhesion factor) or a set of first components is typically attached to a region of the first longitudinal segment and a second component, such as a motile cell (e.g., a phagocytic, a protozoic, a moneran cell, etc.) is generally attached to the first component or to one or more members of the set of first components. The second component is, e.g., optionally fluorescently labeled. A gradient is typically formed from an edge of the second longitudinal segment of the first channel, which induces the second component to detach from the first component or from the one or more members of the set of first components. Thereafter, a detectable signal produced by the detached second component is generally detected. The type of gradient utilized with these methods optionally include a chemical composition gradient, a light energy gradient, a magnetic gradient, a pH gradient, a dissolved oxygen gradient, a temperature gradient, or the like.

The first component or set of first components are optionally attached to the first channel by flowing the first component or the set of first components over the first longitudinal segment of the first channel concomitantly with flowing a third component (e.g., a buffer) over the length of the second longitudinal segment of the first channel. During this step, at least some of the first component or set of first components attaches to the first longitudinal segment. Thereafter, the third component is flowed through the first channel to remove any unattached first component. The second component is typically then flowed through the first channel and in so doing, some of the second component attaches to the attached first component. This step is generally followed by flowing the third component through the first channel to remove any unattached second component.

In one preferred embodiment, the chemical composition gradient is established by concomitantly flowing a third component (e.g., a buffer) and a fourth component (e.g., a chemotactic factor) or a set of fourth components into the first channel in which the fourth component or the set of fourth components forms the gradient from an edge of the second longitudinal segment of the first channel. For example, a buffer is typically flowed from a second channel into the first channel and a chemotactic factor is typically flowed from a third channel into the first channel in which the buffer and the chemotactic factor mix in the first channel to form the gradient of the chemotactic factor. In one embodiment, the concentration of the fourth component or the set of fourths components is highest along a length of the second longitudinal segment that is farthest from the first longitudinal segment and lowest along the length of the second longitudinal segment that is nearest to the first longitudinal segment. In another embodiment, the concentration of the fourth component or the set of fourths components is lowest along a length of the second longitudinal segment that is farthest from the first longitudinal segment and highest along the length of the second longitudinal segment that is nearest to the first longitudinal segment.

As a negative control, e.g., a buffer is optionally flowed into contact with the attached motile cell in the first channel to assess the signal produced in the absence of the chemotactic factor. Additionally, a positive control optionally includes flowing, e.g., a chemotactic factor into contact with the attached motile cell in the first channel to determine the signal produced in the absence of a buffer.

The various components of these methods (e.g., the first, second, third and the fourth or more components) are optionally flowed, e.g., using a fluid direction component including, e.g., a fluid pressure force modulator, an electrokinetic force modulator, a capillary force modulator, a fluid wicking element, and/or the like. The methods optionally further include flowing a modulator into contact with the second component in the first channel prior to introduction of the fourth component in which the modulator modulates (e.g., activates or inhibits) detachment of the second component from the first component or the set of first components.

The detectable signal provides an indication of the gradient induced activity present in the second component and/or an ability of the modulator to modulate the gradient induced activity of the second component. The detectable signal optionally includes a refractive index, a cellular activity, a light emission, an absorbance, a change in absorbance, a fluorescence, a change in fluorescence, a color shift, a fluorescence resonance energy transfer, a radioactive emission, a change in pH, a change in temperature, a change in mass (e.g., by mass spectroscopy), or the like. Additionally, the chemical composition gradient formed by the fourth component or the set of fourth components in the first channel is optionally varied and a resulting increase or decrease in the detectable signal is optionally measured. Furthermore, the concentration of the second component is optionally increased in solution in the first channel as the gradient induces the second component to detach from the first component or the set of first components.

The present invention also relates to methods of detecting a binding activity. For example, a first component is typically flowed (e.g., in a first flow stream) through a first channel (e.g., a microchannel) concomitantly with at least one second component (e.g., in a second flow stream) or a set of second components in which the second component (e.g., an enzyme or a receptor) or the set thereof binds to the first component. Thereafter, the methods include, e.g., detecting a detectable signal that indicates a final concentration of the at least one first component or the set of first components that remains unbound after exiting from the first channel. Optionally, the methods include detecting a detectable signal that indicates an initial concentration of the at least one first component or the set of first components prior to entry of the component or set thereof into a first channel.

The first component or set of first components can diffuse more rapidly in solution than the second component or set of second components. Furthermore, the first channel generally includes a mixing longitudinal segment in which, during the flowing step, the first component or the set of first components diffuse substantially across the first channel in the mixing longitudinal segment, while the second component or the set of second components typically diffuse less than substantially across the first channel in the mixing longitudinal segment. The first and second components are typically flowed through the first channel using fluid direction components that optionally include, e.g., a fluid pressure force modulator, an electrokinetic force modulator, a capillary force modulator, a fluid wicking element, or the like.

As a positive control for detecting a detectable signal, the first component or the set of first components is optionally flowed through the first channel, e.g., in the absence of the second component or the set of second components. A negative control for detecting a detectable signal optionally includes the step of flowing the second component or the set of second components through the first channel, e.g., in the absence of the first component or the set of first components.

The methods also optionally include concomitantly flowing a modulator into contact with the second component in the first channel, in which the modulator modulates (e.g., activates or inhibits) the binding of the second component to the first component. The detected binding activity provides an indication of the binding activity of the second component and/or an ability of the modulator to modulate the binding activity of the second component. Additionally, the first and second detectable signals optionally include, e.g., a refractive index, a cellular activity, a light emission, an absorbance, a change in absorbance, a fluorescence, a change in fluorescence, a color shift, a fluorescence resonance energy transfer, a radioactive emission, a change in pH, a change in temperature, a change in mass (e.g., by mass spectroscopy), or the like.

In one preferred embodiment, the invention provides methods of detecting neurotransporter activity in a cell. In the methods, a first cell or cell set which includes a transporter activity is flowed in a first microscale channel. A selected neurotransmitter and a second cell or second cell set comprising a receptor for the neurotransmitter are flowed into the first channel. A signal produced by contact of the second cell or cells of the second cell set by the neurotransmitter is then detected, thereby determining the rate of transport activity of the transporter in the first cell or cells of the first cell set.

Optionally, the first cell or cell set is flowed into contact with the neurotransmitter prior to contacting any remaining neurotransmitter to the second cell or cell set. A transport inhibitor is optionally added to the microchannel and the resulting modulation in signal intensity produced by the second cell or cell set is measured, thereby determining the activity of the inhibitor on transport activity in the first cell set.

The invention provides devices and systems for practicing the methods noted herein. For example, in one aspect, a device which includes a body structure having at least a first, second and third microscale channel fabricated therein is provided. The first microscale channel typically includes a first component comprising transporter activity which transports at least a first transportable molecule. The second microscale channel intersects the first microscale channel at a first channel intersection. The second microscale channel typically includes a transportable molecule. The third microscale channel intersects the first microscale channel in a second channel intersection region. The third microscale channel includes a second component which binds to the first transportable molecule, causing emission of a detectable signal.

The device optionally includes a source of a modulatory agent such as an inhibitor which inhibits transport of the first transportable molecule by the first component, or an activator which enhances transport of the first transportable molecule. Sources of the other assay components noted herein, such as carrier moieties or sets of carrier moieties (including cells, liposomes, organelles, proteins, protein-lipid complexes, etc.), transportable molecules (proteins, sets of proteins, peptides, sets of peptides, lipids, sets of lipids, carbohydrates, sets of carbohydrates, organic molecules, sets of organic molecules, drugs, sets of drugs, receptor ligands, sets of receptor ligands, antibodies, sets of antibodies, neurotransmitters, sets of neurotransmitters, cytokines, sets of cytokines, chemokines, sets of chemokines, hormones, sets of hormones, etc.) are also optionally incorporated into the devices herein.

Devices optionally incorporate additional elements such as detectors for detecting signals produced in the first channel, e.g., operably connected to a computer for data analysis, fluidic controllers for directing fluid movement in the first channel, one or more transparent detection window fluidly connected to the first channel, robotic armatures for moving the body structure or sample arrays. Systems and devices typically incorporate, or are used in conjunction with, a computer having an instruction set for controlling or processing a signal from the detector, the fluidic controller, the robotic armature or other device or system elements.

The first and second intersections are optionally opposed across the first channel, or at least in a close proximal relationship. This arrangement is advantageous for studying biological diffusion properties of transporters, transportable molecules and transport receptors across small distances, e.g., to examine diffusion properties at, e.g., neural junctions between nerve cells (e.g., axons and dendrites).

In one embodiment, during operation of the device, a mixture of the first component, the second component and the transportable molecule are flowed in the first channel and the device has a detector for detecting a signal produced by the mixture. The detector is typically positioned to detect a signal produced by the mixture at multiple points in the first channel.

The present invention also includes a device or system including a body structure that includes a first microscale channel fabricated therein. The first microscale channel includes a first component (e.g., an adhesion factor) or a set of first components that includes a first attachment activity, in which the first component or set thereof is attached to a region of a first longitudinal segment of the first microscale channel. The first microscale channel also includes a second component (e.g., a motile cell) that includes a second attachment activity in which the second component is attached to the first component or to one or more members of the set of first components. The first microscale channel also includes a third component (e.g., chemotactic factor) or a set of third components that forms a gradient from an edge of a second longitudinal segment of the channel, in which the gradient induces the second component to detach from the first component or the members of the set of first components to produce a detectable signal.

In one embodiment, the depth of the first longitudinal segment differs from the depth of the second longitudinal segment in the first microscale channel of the device. Furthermore, the second component (e.g., a phagocytic cell, a protozoic cell, a moneran cell, etc.) are optionally fluorescently-labeled. The first microscale channel also optionally includes a modulator (e.g., an activator or an inhibitor) that modulates detachment of the second component from the first component.

Additionally, the device or system typically includes a detector in or proximal to the first microscale channel for detecting a signal produced in the first microscale channel that is operably connected to a computer. The device also generally include a fluidic controller for directing fluid movement in the first microscale channel, one or more transparent detection windows fluidly connected to the first microscale channel, a robotic armature for moving the body structure or sample plates relative to the body structure, and/or a source of components (e.g., microwell plates). When the device includes a computer, the computer typically includes an instruction set for controlling or processing a signal from the detector, the fluidic controller, and/or the robotic armature.

During operation of the device, a mixture of the third component (e.g., a chemotactic factor) or, e.g., the set of the third components and a buffer are optionally flowed in the first microscale channel and the device typically further includes a detector for detecting a signal produced by detachment of the second component induced by the third component in the mixture. Alternatively, the device includes a detector for detecting a signal produced by detachment of the second component induced by the third component at multiple points in the first channel.

The present invention also relates to a device or system that includes a body structure including at least a first, second, and third microscale channel fabricated therein. The first microscale channel includes a first and second component or sets thereof in which the second component (e.g., an enzyme or a receptor) binds to the first component. The second microscale channel typically intersects the first microscale channel at a first channel intersection and optionally the second microscale channel includes a second detector in or proximal to the second microscale channel for detecting an initial concentration of the first component. The third microscale channel optionally intersects the first microscale channel at a second channel intersection in which the third microscale channel includes a first detector in or proximal to the third microscale channel for detecting a final concentration of the first component that remains unbound. The first microscale channel of the device also optionally includes a modulator (e.g., an inhibitor) that modulates the second component from binding to the first component.

The first component or set of first components generally diffuses more rapidly in solution than the second component or set of second components. Furthermore, the first channel typically includes a mixing longitudinal segment in which, during operation of the device, the first component or the set of first components diffuse substantially across the first channel in the mixing longitudinal segment, while the second component or the set of second components diffuse less than substantially across the first channel in the mixing longitudinal segment.

The device also optionally includes a fluidic controller for directing fluid movement in the first microscale channel, a transparent detection window fluidly connected to the first microscale channel, a robotic armature for moving the body structure, and/or a source of components. When the device includes a computer, the computer typically includes an instruction set for controlling or processing a signal from the detector, the fluidic controller, and/or the robotic armature.

The invention also provides kits for practicing the methods and utilizing the devices noted herein. For example, the kits of the invention optionally include a first component comprising a transporter activity and a second component which is capable of producing a signal upon exposure to a transportable molecule which is transportable by the first component. The components generally include a carrier moiety or set of carrier moieties, a container for packaging the first or second component, instructions for practicing the methods herein, e.g., using the devices noted herein, one or more reagents for buffering or storing the first or second component, one or more transportable molecule, one or more test compound, a test compound library or the like.

Definitions

Unless otherwise indicated, the following definitions supplement those in the art.

"Transporter activity" refers to movement of a transportable molecule such as a transmitter across a biological barrier such as a cell membrane. This is typically performed by specific transporters or non-specific endocytosis of the transmitter or other transportable molecule. See, e.g., Darnell et al. (1990) *Molecular Cell Biology*, Second Edition Scientific American Books New York, FIGS. 17–38 for an introduction to specific endocytosis of a neurotransmitter. Additional details regarding neurotransporters are found in *Neurotransmitter Transporters: Structure, Function and Regulation* (1997) M. E. A Reith, ed. Human Press, Towata N.J. An example class of transporters are the biogenic amine transporters (e.g., those which transport norepinephrine (NE), dopamine (DA), or serotonin (5-HT), referred to as NET, DAT and SERT), which utilize ionic gradients of $Na^+$, $K^+$ and $Cl^-$ ions to drive transport reactions.

In addition to standard neurotransmitter transporters, transporter activity as used herein optionally includes other systems for translocating transmitters across a cell or other membrane, such as translocation through ionophores or other membrane translocation proteins such as permeases which facilitate transport of materials by mechanisms other than endocytosis. See, e.g., Darnell et al. (1990) Molecular Cell Biology Second Edition Scientific American Books New York, Chapter 15 for an introduction to permeases and other transport facilitating proteins.

A "transmitter" is a transportable molecule which can be transported by the transporter, and/or which can trigger a detectable change on a cell comprising a receptor for the transmitter. Examples include neurotransmitters which transmit a signal across a synaptic junction by binding to a receptor on a post-synaptic cell, where the neurotransmitters are also transported by neurotransmitter transporters.

A "longitudinal segment" includes a segment of a channel (e.g., a microchannel) that extends over at least a substantial portion of the length of the channel.

A "double Y" array is a configuration of channels (e.g., microchannels) in which at least four channels intersect with a first channel, i.e., at least two channels intersect with one end of the first channel and at least two channels intersect with the other end of the first channel.

DETAILED DISCUSSION OF THE INVENTION

Figure 1:
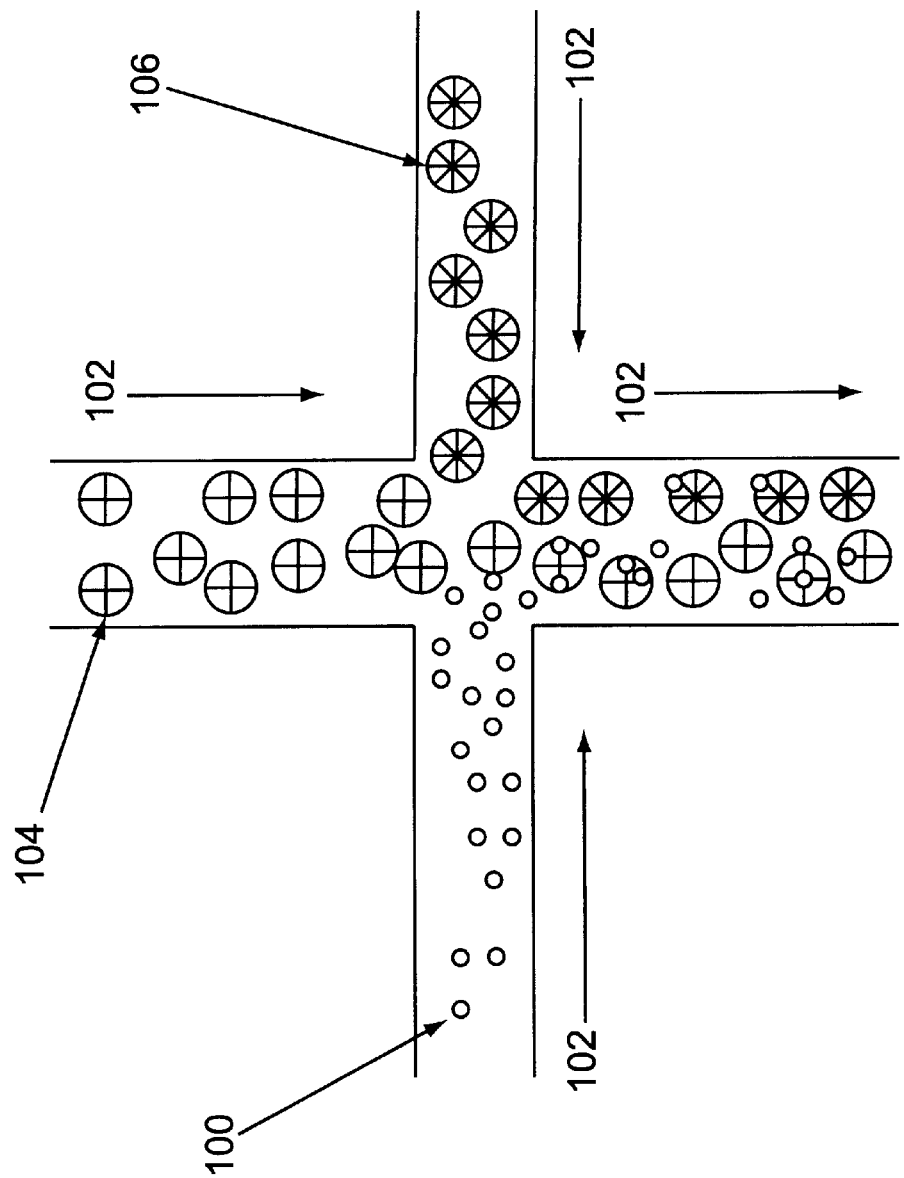
FIG. 1 is a schematic of a microfluidic structure comprising a flow of materials comprising transporter, transmitter, and transmitter-receptor components.

The present invention provides, inter alia, methods and microfluidic systems for modeling various biological processes. For example, the invention is optionally used to model nerve impulse transmissions across synaptic clefts to assess the activity of assorted transporter components, e.g., neurotransmitter transporters. Other processes that are generally modeled using the present invention, include gradient induced activities, e.g., chemotactic responses of motile cells. The invention additionally includes methods and devices for analyzing the binding activities of many different biological constituents, such as enzyme-substrate interactions, receptor-ligand interactions, or other binding interactions. Furthermore, the effect of modulators of these activities also optionally evaluated.

In general, existing techniques for studying transmitters, transporters, and other aspects of cell signaling lack sufficient throughput for modeling transmitter diffusion, transporter activity, transmitter activity, and the like. Additionally, progress in the study of gradient induced responses and binding activities has also been hindered by in vitro systems that also lack high-throughput and whose results have been difficult to quantify. As such, the automated and quantitative assays of the present invention for modeling all of these important biological processes are desirable.

The following provides details regarding the high-throughput microscale systems of the present invention for use in modeling transporter activity, transmitter degradation activity, transmitter activity, cell signaling, and detection of modulators (inhibitors and enhancers) of transporter or transmitter degradation activity. It also provides details relating to high-throughput systems for modeling gradient induced activities and general binding activities. These and many other features which will be apparent upon complete review of the following disclosure.

Transporter Activity

Specific endocytosis of neurotransmitters permits recycling of transmitters released by, e.g., presynaptic cells into a synaptic cleft. In addition to conserving transmitter, this recycling of transmitters regulates the level of a transmitter in the synapse. Thus, transporter activity is central to many cell-signaling biological activities. See, *Neurotransmitter Transporters: Structure, Function and Regulation* (1997) M. E. A. Reith, ed. Human Press, Towata N.J.; and *Neurotransmitter Methods: Methods in Molecular Biology Volume* 72 (1997) R. Rayne, ed. Human Press, Towata, N.J., for a review of transporter and transmitter biology.

The transport of transportable moieties such as certain neurotransmitters serves as an activity regulation point for a variety of cell-signaling events. For example, by sequestering transmitters using ion-dependent transporter activities to drive transport of transmitters, cells comprising transporter activity decrease the concentration of local available transmitter molecules, thereby reducing the amount of transmitter available to bind to cells which have transmitter receptors. Similarly, the local degradation of transmitters, e.g., through activity of an enzyme such as an oxydase or esterase typically have a related biological effect.

In addition to using endocytosis mechanisms such as those driven by transporters which utilize ionic gradients of $Na^+$, $K^+$ and $Cl^-$ ions to drive transport reactions, cells can transport transmitters through the activity of transport facilitating proteins. Transport facilitating proteins can also transport materials into cells. Transport facilitating proteins in biological systems facilitate transport of transportable moieties in at least two different ways. First, many transport facilitating proteins facilitate endocytosis of specific transportable components. Second, some permeases (optionally considered to be transporters herein) assist in passive diffusion of ions or molecules across a membrane by providing a path for the ion or molecule in the membrane. In diffusion, the rate of transport is directly proportional to the concentration gradient across the membrane. Some transporters engage in active transport in which metabolic energy is used to move transportable ions or molecules across a membrane or other biological barrier, including against the concentration gradient of the transportable component. Cellular energy sources and/or ion gradients across cell membranes are used to drive active transport strategies.

The present invention relates to a new assay system for monitoring transporter/transmitter activities in vitro. In one format, cells or other components which comprise transporter activity are flowed through a first microfluidic channel as shown in FIG. 1. Transmitter 100 is flowed (flow direction is indicated by arrows 102) into the first channel from a second channel, while cells or other components comprising receptors to the transmitter are flowed from a third channel into the first channel. If cells/components with transporter activity 104 actively take up transmitter 100, the concentration of transmitter 100 is decreased in the channel as transmitter 100 diffuses across the channel and into contact with cells/components with transmitter receptor 106, thereby reducing transmitter 100 available to bind cells/components with transmitter receptor 106. Typically, activity of transmitter 100 on cells/components with transmitter receptor 106 is assessed by monitoring a transmitter-dependent activity in cells/components with transmitter receptor 106. A variety of receptor-transmitter activities are known. See, *Neurotransmitter Transporters: Structure, Function and Regulation* (1997) M. E. A. Reith, ed. Human Press, Towata N.J., and the references cited therein.

If a transporter modulator is added upstream or concurrent with the transmitter, the modulator can increase (i.e., when the modulator is an activator of transport function) or decrease (i.e., when the modulator is an inhibitor of transport function) the activity of the transporter. Thus, one preferred assay monitors the activity of the transporter in the presence of the modulator by monitoring a transmitter-dependent activity in the cells/components comprising the transmitter receptor. Because of the high-throughput nature of this microscale assay, a large library of compounds can be screened for transporter modulatory activity.

Specific Assay Formats for Transporter Activity Assays

FIG. 1 shows one basic assay format for the present invention. As depicted, cells or other components comprising transporter activity are flowed in a first channel. Transmitter is flowed into the first channel from a second channel, where it contacts the cells or other components comprising transporter activity. The cells comprising transporter activity transport the transmitter, thereby localizing the transmitter within the cells or other components comprising transporter activity. Transmitter which is not localized by transport diffuses into contact with cells or other components which include receptors for the transmitter. Following binding of the transmitter to the cells or other components which include receptors for the transmitter, a detectable signal is produced.

An advantage of this assay format is that it mimics the biological activity of the relevant components (e.g., as noted above) in the assay. For example, the cells comprising transporter activity are analogous to a pre-synaptic cell comprising transporter activity, while the cells comprising a transmitter receptor are analogous to a post-synaptic cell which is activated by the transmitter. The diffusion of the transmitter across the first channel and into contact with the cells comprising a transmitter receptor mimics diffusion of the transmitter across a synapse.

Variations on the above assay are optionally made, depending on the components to be assayed, microfluidic system available, preferences of the investigator and the like. For example, although depicted with cells or components comprising transporter activity, other activities which eliminate the ability of the transmitter to bind to the cells comprising a transmitter receptor are optionally substituted and the effects of modulators can be tested on these activities. The activity of an enzyme which inactivates the transmitter is optionally monitored by substitution of the enzyme for the cells comprising transporter activity, as noted above.

In a configuration desirable for screening potential transport modulator compounds, a modulator is flowed into contact with the cells comprising transporter activity, before, during or after flowing the transmitter into proximity with the cells in the first channel. The transport inhibitory or activating effect of the modulator is typically monitored by assaying for any change in the signal produced by the cell, as compared to signal produced in the absence of the modulator.

The modulator is optionally flowed with the transmitter, the cells comprising the transporter activity, the cells with the transmitter receptor, or from a separate source of modulator. Commonly, potential modulators will be arranged in libraries which are accessed by the microfluidic system, such as in microwell plates or dried on substrates. Knapp et al. "Closed Loop Biochemical Analyzers" (WO 98/45481; PCT/US98/06723) provide a variety of such library accessing strategies for microfluidic systems.

When the modulator is flowed from a source distinct from the other assay components, the microfluidic system will, commonly, include an additional modulator flow channel which intersects the flow path of the cells which comprise transporter activity. The modulator compounds are typically incubated with the cells while under flow in a channel, or separately in a chamber or well. The modulator compounds are also, commonly, incubated with the cells prior to introduction into the first channel, e.g., in a microtiter dish, or a well integrated into the body structure comprising the microscale channel.

Commonly, reagents facilitating transport are flowed concomitantly or separately with the components comprising transport activity, depending on the intended assay. For example, buffer comprising ions such as sodium, potassium or calcium are flowed into contact with components comprising transport activities which depend on the presence of these ions for transporter function. For a description of common ion-dependent transporters, and a description of other reagent and buffer conditions for transporter activity, see, *Neurotransmitter Transporters: Structure, Function and Regulation* (1997) M. E. A. Reith, ed. Human Press, Towata N.J., and the references cited therein.

Transmitters, Transporters and Transmitter Receptors

A wide variety of signal transduction systems have been extensively characterized and are optionally applied to the assays of the invention. The basic transmitter, transporter and transporter receptor elements (or cells or other components comprising these activities) are commercially available or can be obtained using known techniques. For example, the 1998 CALBIOCHEM Signal Transduction Catalog and Technical resource lists over 2100 commercially available products related to signal transduction, including G-protein related products, calcium metabolism related products, cytokines, growth factors and hormones, cell adhesion/extracellular matrix tools, protein kinases, protein phosphatases, enzymes, substrates and probes, enzyme activators, enzyme inhibitors, reagents for nitric oxide research, oxidative stress and free radicals, ionophores, neurochemicals, neurotoxins, and neurotrophins, immunophillins, bioactive lipids, cell cycle and apoptosis components, and the like. Similarly, a number of texts describe transmitter and transporter systems, as well as providing information relevant to assays, cell growth and supplies of cells, and other features relevant to the present invention, including: *Neurotransmitter Transporters: Structure, Function and Regulation* (1997) M. E. A. Reith, ed. Human Press, Towata N.J.; *Neurotransmitter Methods: Methods in Molecular Biology Volume* 72 (1997) R. Rayne, ed. Human Press, Towata, N.J.; *Neuropeptide Protocols: Methods in Molecular Biology Volume* 73: Irvine and Williams, eds., Human Press, Towata N.J.; *Neurochemistry: A Practical Approach, $2^{nd}$ edtion* (1997) Turner and Bachelard, eds., Oxford Press, Oxford England; and, *Neural Cell Culture: A Practical Approach* (1996) Cohen and Wilkins, eds. Oxford Press, Oxford England.

One of skill can adapt available cells and reagents to the present invention by providing the cells and reagents to the microfluidic systems herein as noted. Assay conditions and buffer and reagent parameters utilizing transport modulators, transmitters, transporters and the like are typically selected based upon established activity levels, transmitter-transporter pairings, concentrations and kinetic information for known transporters and transmitters, modified by the addition of a selected modulator to the system. Initial screens of a particular putative modulator are optionally conducted at a single concentration of modulator in the system, or at multiple modulator concentrations. Typically, compounds which have modulatory activity based upon an initial screen are titrated into contact with the transporter (or other assay component, as appropriate), in increasing or decreasing amounts, to establish a dose-response curve for the modulator.

Rather than simply using cells which naturally comprise transporters and transmitter receptors in the assays noted herein, recombinant cells are also optionally constructed which include desired transporters or transmitter receptors. This is advantageous because certain cells can be easily maintained in culture using established methods.

Methods of making recombinant cells and expressing cellular proteins such as transport facilitating proteins and transmitter receptors are well known in the art. For an introduction to recombinant methods, see, Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (2nd ed.), Vol. 1–3, Cold Spring Harbor Laboratory, Cold Spring Harbor, N.Y., 1989 ("Sambrook"); and *Current Protocols in Molecular Biology*, F. M. Ausubel et al., eds., Current Protocols, a joint venture between Greene Publishing Associates, Inc. and John Wiley & Sons, Inc., (supplemented through 1999) ("Ausubel"). Culture of mammalian cell lines and cultured cells from tissue or blood samples is well known in the art. Freshney (*Culture of Animal Cells, a Manual of Basic Technique, Third Edition*, Wiley-Liss, New York (1994)) and the references cited therein provides a general guide to the culture of animal cells. Culture of plant cells is described in Payne et al. (1992) *Plant Cell and Tissue Culture in Liquid Systems*, John Wiley & Sons, Inc., New York, N.Y. Additional information on cell culture, including prokaryotic cell culture, is found in Ausubel, Sambrook and Berger, supra. Cell culture media are described in Atlas and Parks (eds) *The Handbook of Microbiological Media* (1993) CRC Press, Boca Raton, Fla. Additional information is found in commercial literature such as the Life Science Research Cell Culture catalogue (1998) from Sigma-Aldrich, Inc (St Louis, Mo.) and, e.g., the Plant Culture Catalogue and supplement (1997) also from Sigma-Aldrich, Inc (St Louis, Mo.). Additional details on the cloning and expression of transporters is found in *Neurotransmitter Transporters: Structure, Function and Regulation* (1997) M. E. A. Reith, ed. Human Press, Towata N.J.; *Neurotransmitter Methods: Methods in Molecular Biology Volume* 72 (1997) R. Rayne, ed. Human Press, Towata, N.J.; *Neuropeptide Protocols: Methods in Molecular Biology Volume* 73: Irvine and Williams, eds., Human Press, Towata N.J.; *Neurochemistry: A Practical Approach*, $2^{nd}$ *edition* (1997) Turner and Bachelard, eds., Oxford Press, Oxford England; and, *Neural Cell Culture: A Practical Approach* (1996) Cohen and Wilkins, eds. Oxford Press, Oxford England.

Modulators

Essentially any molecule can be tested for transporter modulatory activity, gradient induced modulatory activity, or binding modulatory activity. Further, essentially any chemical compound can be used as a potential modulator in the assays of the invention, although most often compounds which can be dissolved in aqueous or organic (e.g., DMSO-based) solutions are used to facilitate flow in microscale systems. The assays herein are designed to screen large chemical libraries by automating the assay steps and providing compounds from any convenient source to the assays. It will be appreciated that there are many suppliers of chemical and biological compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial library containing a large number of potential transport activity modulator compounds ("potential modulator compounds"). Such "combinatorial chemical libraries" are screened in one or more assays, as described herein, to identify those library members (particular chemical species or subclasses) that display a desired characteristic activity. The compounds thus identified can serve as conventional "lead compounds" or can themselves be used as potential or actual therapeutics for treating conditions amenable to treatment by modulating transporter activities. As noted, a variety of diseases are treated by administering transport modulators, including: panic, stress, obsessive compulsive disorders, depression, chronic pain and many other physical and psychological conditions. See, *Neurotransmitter Transporters: Structure, Function and Regulation* (1997) M. E. A. Reith, ed. Human Press, Towata N.J., and the references cited therein.

A typical combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way, or a selected way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. J. Pept. Prot. Res. 37:487–493 (1991) and Houghton et al., Nature 354:84–88 (1991)). Other chemistries for generating chemical diversity libraries are also optionally used. Such chemistries include, but are not limited to: peptoids (PCT Publication No. WO 91/19735), encoded peptides (PCT Publication WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., Proc. Nat. Acad. Sci. USA 90:6909–6913 (1993)), vinylogous polypeptides (Hagihara et al., J. Amer. Chem. Soc. 114:6568 (1992)), nonpeptidal peptidomimetics with α-D-glucose scaffolding (Hirschmann et al., J. Amer. Chem. Soc. 114:9217–9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (see, Berger and Kimmel, *Guide to Molecular Cloning Techniques, Methods in Enzymology*, volume 152, Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, N.Y., (Sambrook); and *Current Protocols in Molecular Biology*, F. M. Ausubel et al., eds., Current Protocols, a joint venture between Greene Publishing Associates, Inc. and John Wiley & Sons, Inc., (e.g., current through 1999, e.g., at least through supplement 37) (Ausubel)), peptide nucleic acid libraries (see, e.g., U.S. Pat. No. 5,539,083), antibody libraries (see, e.g., Vaughn et al., Nature Biotechnology, 14(3):309–314 (1996) and PCT/US96/10287), carbohydrate libraries (see, e.g., Liang et al., Science, 274:1520–1522 (1996) and U.S. Pat. No. 5,593,853), small organic molecule libraries (see, e.g., benzodiazepines, Baum C&EN, Jan. 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

Control reactions which measure the activity of the selected transporter which does not include a modulator are optional, as the assays are highly uniform. Such optional control reactions are generally appropriate, however, and increase the reliability of the assay(s). Accordingly, in a preferred embodiment, the methods of the invention include a control reaction (or reactions). For each of the assay formats described, "no modulator" control reactions which do not include a modulator provide a background level of transporter activity.

In some assays, it is desirable to have positive controls to ensure that the components of the assays are working properly. At least two types of positive controls are appropriate. First, a known transport modulator is optionally flowed into contact with components comprising transport activities, and the resulting affects on transporter activity monitored. Examples of known modulators include paraxetine, citalopram, fluxetine, imipramine, amitriptyline, mazindol, cocaine, desipramine, nomifensine, GBR12909, D-amphetamine, L-amphetamine, nortriptyline, DA, $MPP^+$, NE, 5-HT, β-PMA, TIA, 4β-PDBu, ConA, Mezerein, Histamine, Impromidine, Dimaprit, PEA, SNP, EGTA, Thapsigargin, Genistein, MHC, NECA, N6-CPA, 8-Br-cGMP, SNAP, Hydroxylamine, Calmidazolium, LY-83583, Methylene blue, CGS9343B, DOI, Interferon-alpha, and combinations thereof. See, Reith, supra.

Second, a known general inhibitor of cellular activity is optionally added, and the resulting decrease in transporter activity similarly detected. It will be appreciated that modulators are also optionally combined in assays with known transport activators or inhibitors to find modulators which inhibit activation or repression of transporter activity by the known activator or inhibitor.

Gradient Induced Activity

Model systems that mimic biological processes such as gradient induced activities are of increasing importance, e.g., in pharmacology, immunology, and the like. However, as mentioned above, progress in the study of gradient induced activities (e.g., chemotaxis) has been impeded by in vitro assays that are, inter alia, tedious to perform. Furthermore, the results produced by these assays have been difficult to quantify. The present invention addresses these shortcomings in the prior art by providing automated and quantitative assays that are optionally used to model essentially any gradient induced activity.

In particular, embodiments of the present invention that are used to assay gradient induced activities (e.g., chemotactic responses) generally include simultaneously flowing an adhesion factor and a buffer into a microchannel such that the adhesion factor binds to at least a substantial portion of a longitudinal segment of the microchannel. Thereafter, a suspension of motile cells (e.g., fluorescently-labeled cells) is typically flowed into the channel in which some of the cells generally adhere to the adhesion factor. Unbound cells are optionally washed away. Following these preparatory steps, a gradient of, e.g., a selected test compound is typically established in the channel by flowing the compound into the channel simultaneously with a buffer. If the test compound induces a response, cells will migrate off the adhesion factor and be swept down the channel in a fluid stream that pass through a detector where a detectable signal produced by the cells (e.g., flluorecence) is detected.

As discussed, the present invention relates in part to methods of detecting a gradient-induced activity. The methods include providing a first channel (e.g., a microchannel) with an internal surface that typically includes a first and a second longitudinal segment. Longitudinal segments extend lengthwise within the channel. Optionally, the internal surface includes three or more longitudinal segments. A longitudinal segment optionally extends over at least a substantial portion of one, two, three or all four walls of a channel that includes a square, rectangular, or other polygonal cross-sectional area. Alternatively, a longitudinal segment optionally includes, e.g., about $\frac{1}{10000}$, $\frac{1}{1000}$, $\frac{1}{100}$, $\frac{1}{10}$, $\frac{1}{5}$, $\frac{1}{4}$, $\frac{1}{3}$, $\frac{1}{2}$, or more or less of the axial cross-sectional area of the channel and extends over at least a substantial portion of the length of the channel. Other variations are conceivable so long as the longitudinal segment extends over a substantial portion of the length of the channel and includes a portion of the internal cross-sectional perimeter and/or internal cross-sectional area of the channel.

For example, an adhesion factor is generally attached to the first longitudinal segment and a motile cell (e.g., a phagocytic, a protozoic, a moneran, or other cell) is typically attached to the adhesion factor. Thereafter, a gradient is typically established in the second longitudinal segment of the first channel. The gradient can induce the motile cell to detach from the adhesion factor to produce a detectable signal that is detected. Various types of gradients are suitable for use with these methods including a chemical gradient, a light energy gradient, a magnetic gradient, a pH gradient, a dissolved oxygen gradient, a temperature gradient, or the like.

Many adhesion factors are known and are optionally used in detecting gradient induced activities, including those from the cadherin family (e.g., B-cadherin, E-cadherin, N-cadherin, P-cadherin, etc.), the selectin family (e.g., L-selectin, P-selectin, E-selectin, etc.), the mucin-like family (e.g., GlyCAM-1, CD34, PSGL-1, MAdCAM-1, etc.), the integrin family (e.g., α4β1, VLA-4, LPAM-1, α4β7, LPAM-1, α6β1, VLA-6, αLβ2, LFA-1, αMβ2, Mac-1, αXβ2, CR4, p150/95, etc.), the immunoglobulin superfamily (ICAM-1, ICAM-2, ICAM-3, VCAM-1, LFA-2, CD-2, LFA-3, CD58, MAdCAM-1, etc.), or the like. There are also many known chemotactic factors that are suitable for use in these methods including an antigen, a set of antigens, a protein, a set of proteins, a peptide (e.g., an acetyl-proline peptide, a fibrino peptide, an N-formyl peptide, etc.), a set of peptides, a lipid (e.g., a prostaglandin, a prostacyclin, a thromboxane, a leukotriene, PAF etc.), a set of lipids, a carbohydrate (e.g., a maltose, a galactose, a glucose, a ribose, etc.), a set of carbohydrates, an inorganic molecule (e.g., a chlorinated benzene, a phosphate, etc.), a set of inorganic molecules, an organic molecule (e.g., citrate, ATP, etc.), a set of organic molecules, a drug, a set of drugs, a receptor ligand, a set of receptor ligands, an antibody, a set of antibodies, a neurotransmitter, a set of neurotransmitters, a cytokine, a set of cytokines, a chemokine (e.g., monocyte chemoattractant protein-1, monocyte chemoattractant protein-2, monocyte chemoattractant protein-3, monocyte inflammatory protein-1 alpha, monocyte inflammatory protein-1 beta, RANTES, I309, R83915, R91733, HCCl, T58847, D31065, T64262, MIP-1b, T39765, NAP-2, ENA-78, IL-1, IL-6, IL-8, Gro-a, Gro-b, Gro-c, IP-10, GCP-2, NAP-4, SDF-1, PF4, MIG, etc.), a set of chemokines, a hormone, a set of hormones, or the like.

Chemotaxis Detection

In one embodiment of the methods of detecting a gradient induced activity, the applicable gradient is a chemical gradient. Chemotaxis is the migration of motile cells up a concentration gradient of a chemotactic factor. Chemotaxis plays a major role in the recruitment of the appropriate immune cells to the site of an infection. Although it has long been known to be an important biological function, in vitro assays for chemotaxis are tedious and difficult to quantify. As such, an automated and quantitative assay for chemotaxis would be very useful.

There are many references that can be consulted regarding chemotaxis-related subject matter appropriate to the methods disclosed herein, including chemotactic agents and target cells. These references include Agree, A. (1994) "Lymphocyte Recirculation and Homing: Roles of Adhesion Molecules and Chemoattractants" *Trends Cell Biol.* 4:326, Bargatze, R. F. et al. (1995) "Distinct Roles of L-Selectin and Integrins α4β7 and LFA-1 in Lymphocyte Homing to Peyer's Patch-HEV In Situ: The Multistep Model Confirmed and Refined" *Immunity* 3:99, Grey, H. et al. (1989) "How T Cells See Antigen" *Sci.Am.* 261(5):56, Bradley, L. M. and Watson, S. R. (1996) "Lymphocyte Migration Into Tissue: The Paradigm Derived From CD4 Subsets" *Curr. Opin. Immunol.* 8:312; Dianzani, U. and Malavasi, F. (1995) "Lymphocyte Adhesion to Endothelium" *Crit. Rev. Immunol.* 15:167, Hogg, N. and Berlin, C. (1995) "Structure and Function of Adhesion Receptors in Leukocyte Trafficking" *Immunol. Today* 16, Hynes, R. O. (1994) "The Impact of Molecular Biology on Models for Cell Adhesion" *Bioessays* 16:663; and Hynes, R. O. (1992) "Contact and Adhesive Specificities in the Associations, Migrations, and Targeting of Cells and Axons" *Cell* 16:303. See also, Kuby, *Immunology, b $3^{rd}$* Ed. W. H. Freeman and Company, New York (1997), Pigott and Power, *The Adhesion Molecule: Facts Book,* Academic Press Inc., San Diego (1993), and Rot, *The Molecular Biology of Leukocyte Chemotaxis*, Chapman and Hall, London (1998).

The present invention includes the material handling advantages of performing analysis and quantification of chemotaxis in a microfluidic processor or chip. Any arrangement of one or more microchannels (i.e., microscale channels) in such a processor are optionally used so long as a response to a gradient can be detected. The microfluidic devices or systems prepared in accordance with the invention typically include at least one microchannel, usually at least two intersecting microchannels, and often, three or more intersecting microchannels disposed within a single body structure. Channel intersections can exist in a number of formats, including cross intersections, "T" intersections, "Y" intersections, or any number of other structures in which at least two channels can be in fluid communication.

Figure 4:
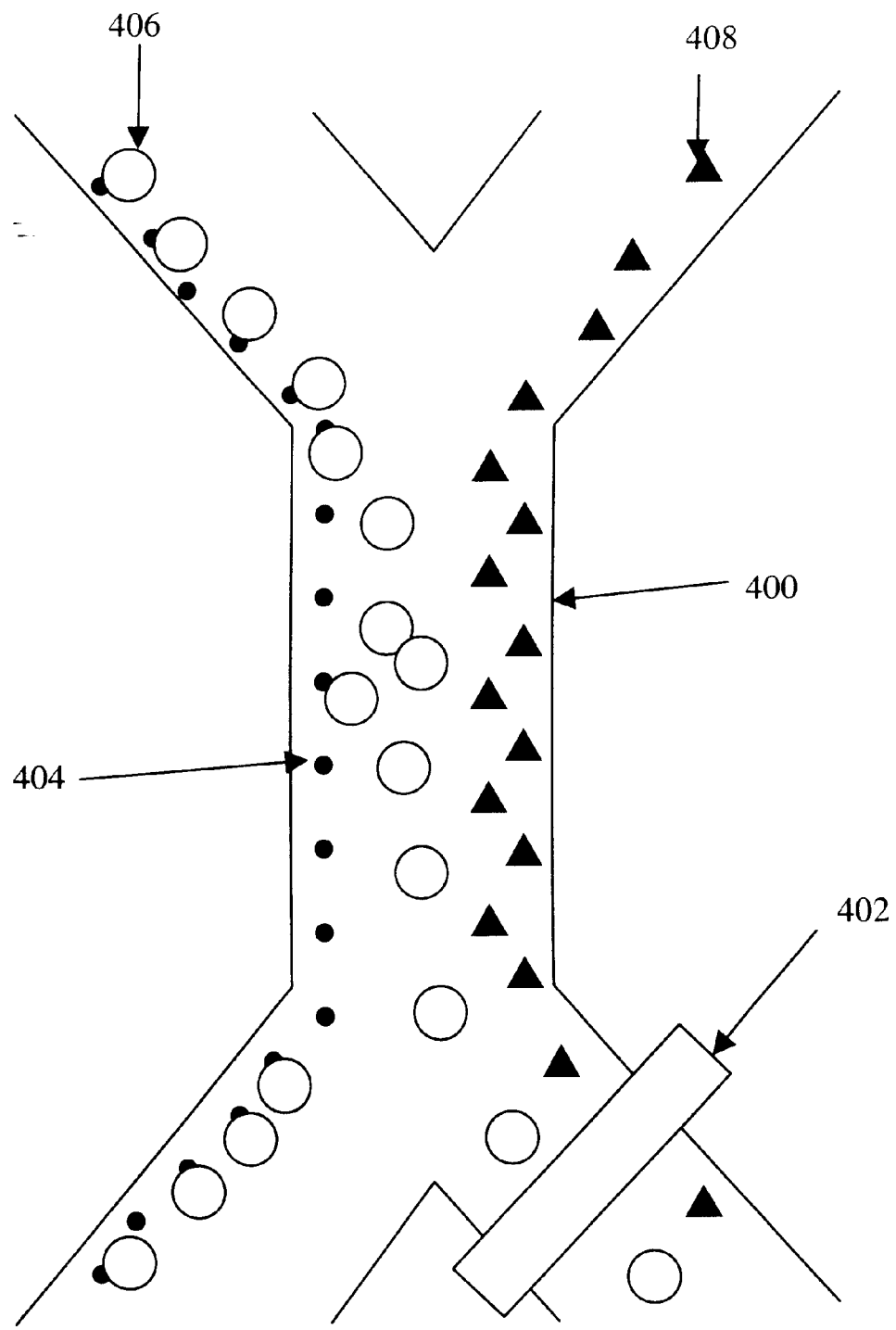
FIG. 4 depicts one embodiment of the device for detecting a gradient induced activity.

In one embodiment shown in FIG. 4, simple double Y microfluidic processor 400 is optionally used to quantify chemotaxis. Motile cells 406 require specific adhesion factors or molecules 404 on a surface in order to move along that surface. The appropriate adhesion factor is generally flowed down the left side of the double Y structure with concomitant flow of buffer down the right side of the structure. For many adhesion factors, nonspecific binding to glass is sufficient to get cells to adhere to the coated surface. The adhesion factor is then typically washed out, resulting in a channel in the middle of the chip where there is adhesion factor bound to the left side, but none on the right side (of course, this arrangement is optionally reversed, or a top/bottom arrangement of components is optionally used). Cells are then typically flowed in and followed by a wash with buffer. The cells will attach to the left side of the channel where there is adhesion factor, but the right side of the channel will not contain cells.

By balancing the flows from the two top reservoirs with those to the two bottom reservoirs, two parallel streams are formed which contact each other in the central channel and diverge into the two wastes. Introduction of chemotactic factor 408 into the upper right channel and buffer into the upper left channel will cause a gradient of chemotactic factor to form across the channel, with a high concentration on the right and a low concentration on the left. If the cells respond to the chemotactic factor they migrate to the right side on the channel. When they migrate off of the adhesion factor, they are swept away in the flowing stream, and travel down the bottom right channel past a cell detection region to a waste well. The rate at which cells pass detector 402 as a function of the established concentration gradient of chemotactic factor allows for quantification of chemotaxis, and the study of modulators, e.g., inhibitors, of chemotaxis by adding those modulators to the flowing stream.

Figure 5:
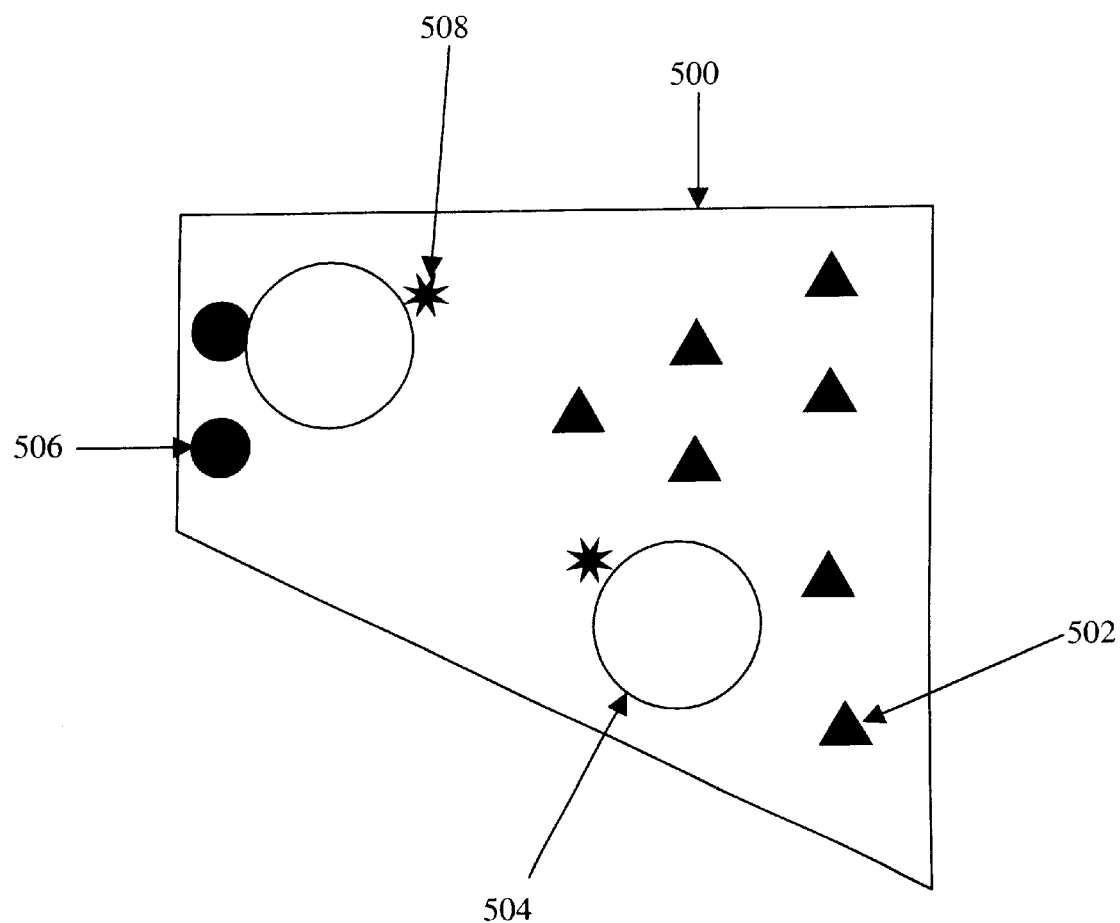
FIG. 5 shows a cross-sectional view of a microchannel from an additional embodiment of the device for detecting a gradient induced activity.

FIG. 5 depicts an alternative mode of detecting a chemotactic response in which motile cells 504 are fluorescently labeled with label 508 (e.g., fluorescein, rhodamine, and the like). Additionally, the bottom of channel 500 is optionally sloped, i.e., deeper on one side than on the other. In turn, as cells migrate off of adhesion factor 506 towards chemotactic factor 502, they go into or out of the detector's plane of focus, and thus increase or decrease their detected fluorescence.

Binding Affinity Detection

Binding interactions are replete in nature. For example, immune responses can involve membrane-bound (e.g., on B cells) or non-membrane-bound antibodies binding to specific antigens. As mentioned above, synaptic junctions typically involve transporters or receptors on post-synaptic neurons, e.g., binding to various neurotransmitters. Additionally, myriad enzyme-substrate binding interactions are known. The study of these interactions has been hampered by the lack of simple and reliable assays. However, the present invention provides methods and devices that are optionally used to easily assess the binding affinity or association constant ($K_a$) of essentially any small or rapidly diffusing molecule (i.e., a ligand or a target) with essentially any large or slowly diffusing molecule or complex of molecules (i.e., a binding agent).

The binding affinity assays of the present invention provide various advantages. For example, binding affinity is optionally analyzed without labeling binding agents or ligands, e.g., with colorimetric, fluorescent, radioactive, or other tags. Additionally, the assays include very low consumption of ligand and binding agents. Typically, the maximum consumption of ligand is about one picomole, e.g., with a ligand flow rate of 1 nl/sec, a run time of 30 seconds, and a ligand concentration of 40 $\mu$M (i.e., 1 nl/sec*30 sec*40 $\mu$M), while the maximum binding agent consumption is also about one picomole, e.g., with a binding agent flow rate of 1 nl/sec, a run time of 10 seconds, and a binding agent concentration of 100 $\mu$M (i.e., 1 nl/sec*30 sec*100 $\mu$M). Other advantages include the ability to assess the $K_a$s of a series of ligands for a given binding agent or target, or the $K_a$s of a series of binding agents with a given ligand in rapid succession under the control of an automated or integrated system. Integrated systems are discussed in greater detail below. Furthermore, resulting $K_a$ values are thermodynamically meaningful, accurate, and reproducible.

In particular, the binding assays of the present invention optionally include detecting an initial concentration of a selected labeled or unlabeled test ligand prior to flowing the ligand into a microchannel with a binding agent (e.g., a biological receptor, an enzyme, a receptor, a protein, a cell, a membrane, a lipid, a nucleic acid, etc.) which is typically much larger in size than the ligand. In the laminar flow streams of the microfluidic devices of the invention, diffusion between streams is generally only significant for the smaller ligand molecules. As such, when the ligand and binding agent are flowed from separate channels into a single microchannel, only the ligand will substantially diffuse into the stream flowing the binding agent. This "one-way" diffusion is optionally further ensured by adjusting the length of the channel in which simultaneous flow occurs. Thereafter, the ligand flow stream is typically flowed into another channel and through a detector to determine a final ligand concentration. The difference between the initial and final ligand concentrations are typically used to derive an indication of binding activity.

Figure 6:
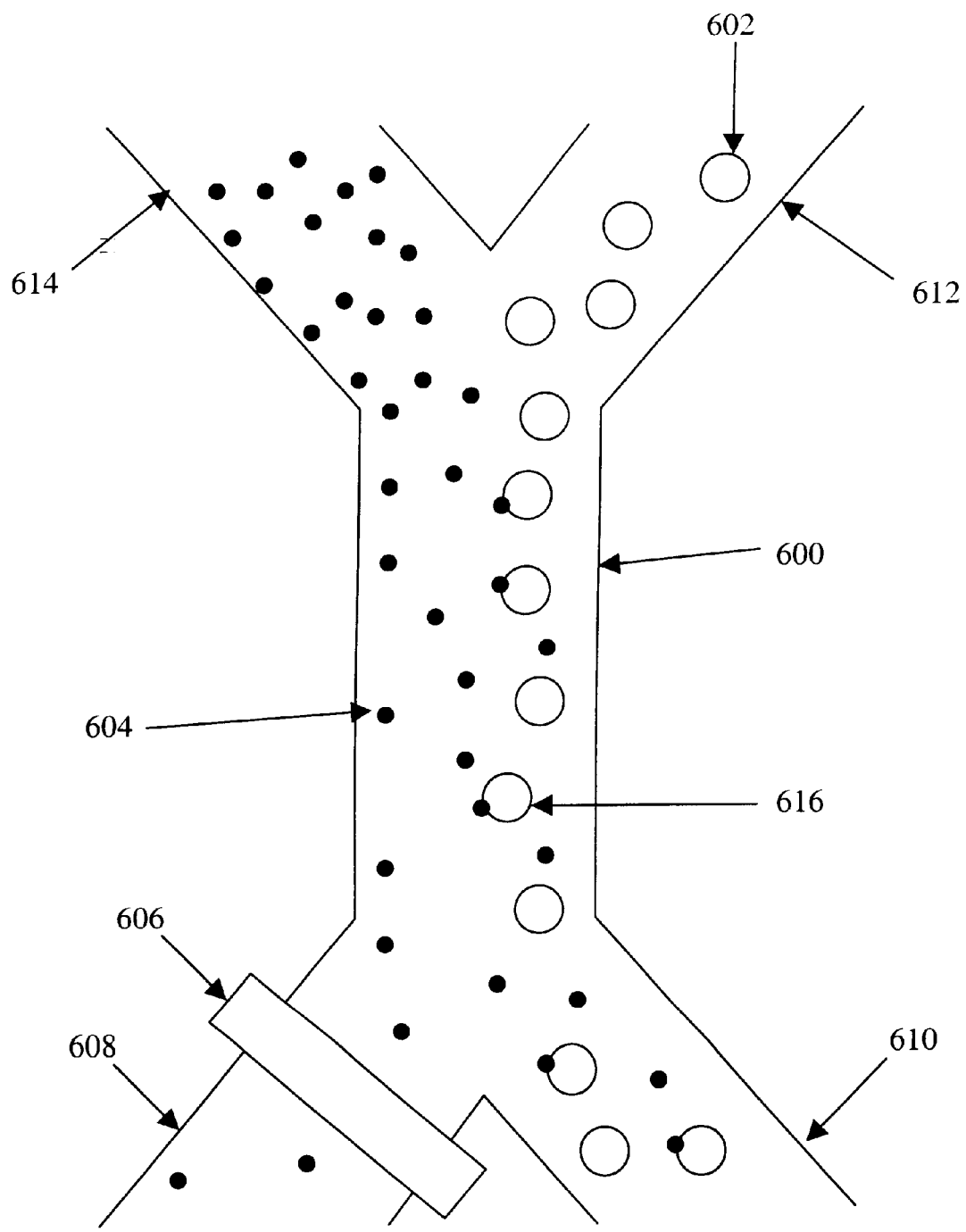
FIG. 6 depicts a microfluidic device for detecting binding activity.

As discussed, the present invention also includes methods relating to the detection of various binding activities, including unlabeled protein-ligands. Although these methods are applicable to any detection mode, absorption or refractive index, and mass spectroscopic detection are preferred modes, because no labeling is necessary. As shown in FIG. 6, ligand 604 is generally flowed into first channel 600 from second channel 614. Binding agent 602 (e.g., an enzyme, a receptor, a cell, a nucleic acid, etc.) is typically also be flowed into first channel 600 from third channel 612 concomitant with ligand 604. Although not shown, a buffer is optionally flowed into first channel 600 from third channel 612, while binding agent 602 is alternatively flowed into first channel 600 from one or more other channels which intersect with first channel 600 downstream from third channel 612 and second channel 614. See also, FIG. 8. As depicted, ligand 604 is typically smaller (i.e., lower molecular weight, smaller surface area, etc.) than binding agent 602 such that ligand 604 generally diffuses more rapidly in solution than binding agent 602. In turn, as ligand 604 and binding agent 602 flow in first channel 600, only ligand 604 diffuses substantially across first channel 600, while binding agent 602 remains substantially undiffused as it flows through first channel 600.

When ligand 604 diffuses across first channel 600, binding agent 602 can bind to ligand 604 to form binding agent-ligand complex 616. (FIG. 6). Once ligand 604, binding agent 602, and binding agent-ligand complex 616 flow to the end of first channel 600, they exit first channel 600 via fourth channel 610. Only ligand 604 also exits first channel 600 via fifth channel 608 and therein detector 606 typically detects a detectable signal that indicates a final concentration of ligand 604 that remains unbound. Although not shown, detectors are also optionally located in or proximal to channels 610, 612, and/or 614, or are fluidly coupled to the channels (e.g., in the case of mass spectroscopy). An advantage of these methods is that they enable one to directly extract the percent ligand 604 bound to binding agent 602 without knowing anything about the spectral properties of ligand 604 and without labeling binding agent 602.

As shown in FIG. 6, the binding assay provided by the present invention optionally utilizes a double Y array on a chip. This figure illustrates a simple example, other embodiments include, e.g., multiple interconnected double Y microchannel configurations, e.g., for use in extracting selected molecules or other compounds. In any case, as shown in FIG. 6, a first step typically involves calibrating ligand 604 concentration to 100 percent. In the embodiments where ligand concentrations are detected both prior to entry into (i.e., $D_1$) and after exit from (i.e., $D_2$) first channel 600, this is optionally accomplished by flowing the initial concentration of ligand 604, $[L]_I$, to be used in the particular experiment, through first channel 600 in the absence of binding agent 602 to be used (i.e., [E]=0). The ratio of signals ($D_2/D_1$) which is the calibrated signal, $D_{cal}$, is then typically set to 100%. To measure binding, one generally first flows the concentration of binding agent 602 to be used in the experiment through the first channel (i.e., $[E]_I$) until it equilibrates (i.e., for $t_{eqb}$). Thereafter, one typically flows $[L]_I$ through the first channel and measures the concentration of L at each detector and calculates $D_{exp}=D_2/D_1$. The mole fraction of L bound to E is generally estimated as follows: $[1-(D_{exp}/D_{cal})]*100\% \propto (\%$ bound). Furthermore, one typically assumes fast $k_{on}$ and $k_{off}$ for the initial evaluation.

There are various parameters that are generally applicable to the methods of detecting binding activity. For example, the binding activity is optionally detected at a temperature in the range of from about 0 to about 100° C. (e.g., for certain thermophilic cell based applications), or e.g., commonly in the range of from about 10 to about 40° C. for typical physiological assays (e.g., those at about 37° C.), in the range of from about 20 to about 30° C. (e.g., for room temperature assays), or e.g., at about 20–25° C. The first component or the set of first components typically diffuses in the range of from about 1.5 to about 100 or more times (e.g., 3, 5, 10, 15, 25, 40, 60, 75, or more times) faster in solution than the second component or the set of second components. For example, the first component or the set of first components typically diffuses about 50 times faster in solution than the second component or the set of second components. In addition, the initial concentration of the ligand prior to entry into the first channel is optionally, e.g., in the range of from about 1 nM to about 1 mM, in the range of from about $10^{-2}$ μM to about 100 μM, or at about 10 μM depending on the assay at issue. Also, the ligand optionally has a molecular weight in the range of from about 200 to about 2000 daltons, in the range of from about 300 to about 1500 daltons, e.g., from about 500 to about 1200 daltons, or is about 1000 daltons. The ligand also typically has a diffusional coefficient in the range of from about $10^{-12}$ to about $10^{-4}$ cm$^2$s$^{-1}$, in the range of from about $10^{-7}$ to about $10^{-5}$ cm$^2$s$^{-1}$, or has one at about $10^{-6}$ cm$^2$s$^{-1}$. Additionally, when the binding agent to be used is an enzyme, it typically has a concentration in the range of from about 1 nM to about 1 mM, in the range of from about $10^{-2}$ μM to about 100 μM, or is at about 10 μM depending, e.g., on the activity of the enzyme relative to the substrate of interest. Furthermore, an enzymatic binding agent also typically includes a molecular weight in the range of from about 10 to about 200 kilodaltons, in the range of from about 20 to about 40 kilodaltons, or is about 30 kilodaltons.

Figure 8:
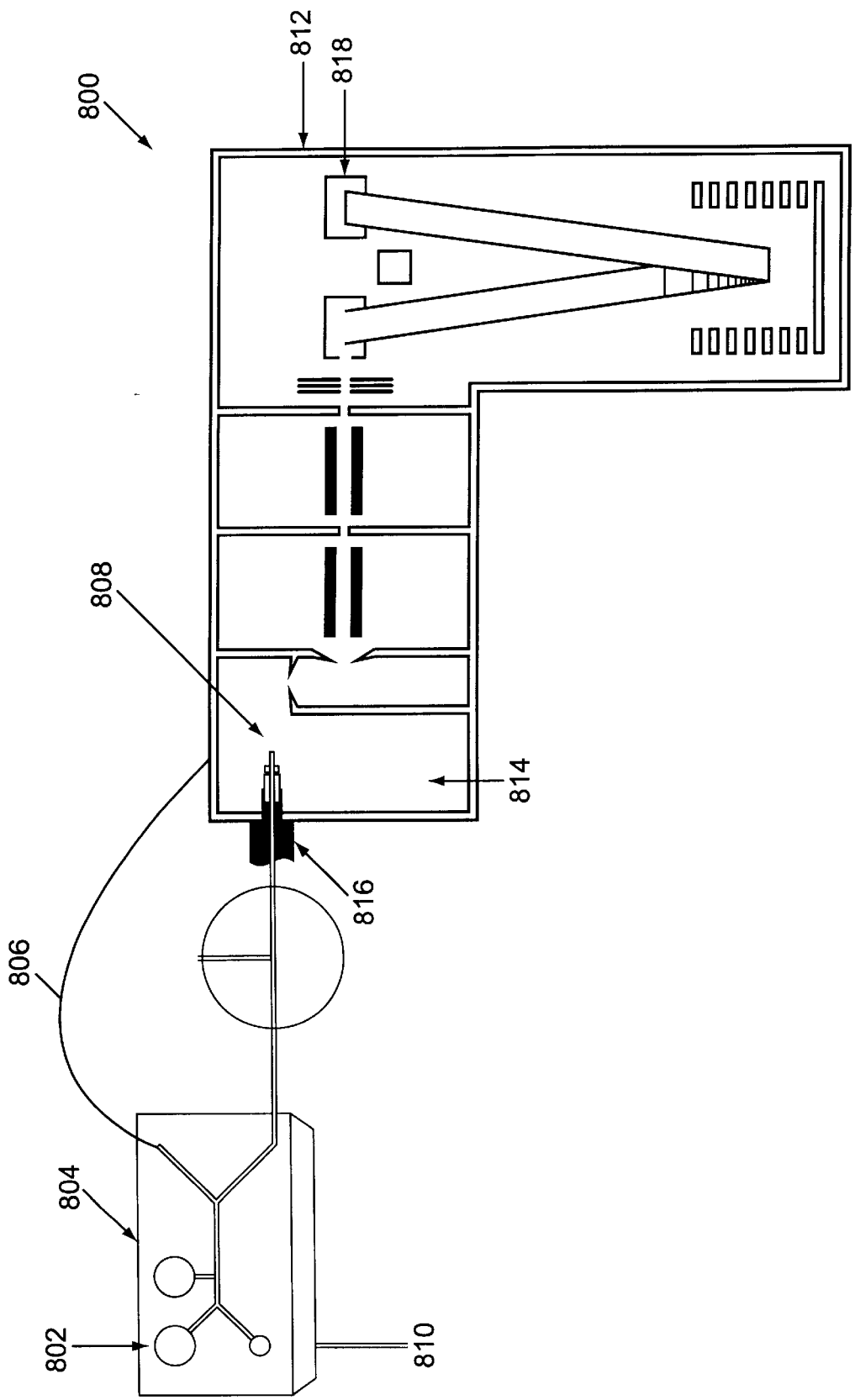
FIG. 8 is a schematic showing an interface between a microfluidic device used in binding affinity assays and electrospray ionization mass spectrometer.

FIG. 8 is a schematic of an interface between a microfluidic device that is optionally used to perform binding affinity assays and an electrospray ionization (ESI) mass spectrometer. As shown, binding assay system 800 includes a microfluidic device that includes a channel network and capillary channel 810 extending from the body of the device. Capillary channel 810 is typically used to draw samples or reagents (e.g., binding agents, ligands, buffers, or the like) from, e.g., the wells of a microwell plate into the device. Although not shown, the body structure optionally includes more than one capillary channel. During operation, buffer is optionally flowed, e.g., from buffer well 802, while binding agent (e.g., proteins, receptors, etc.) is optionally flowed from binding agent well 804. The flow of binding agent from binding agent well 804 is optionally switchable on and off. As also shown, the microfluidic device also interfaces with waste line 806 through which fluids are optionally directed to waste. Examples of device operation are discussed below. The system also includes, e.g., time of flight (TOF) mass analyzer 812, electrospray ionization ion source 814, system inlet 816, and detector 818 which are under vacuum 808. Vacuum 808 is typically set to allow flow rates in the range of from about 0.5 to about 5 nL per second. A preferred flow rate is about 1 nL/s. As mentioned, operational flow rates and channel dimensions are optionally designed such that the binding agent diffuses less than half the width of the main assay channel by the time it reaches the end of the channel and is directed to waste. Binding assay system 800 also includes a switch for rapidly switching between flow from buffer well 802 and flow from binding agent well 804.

As mentioned, essentially any molecule is optionally used as a ligand for these methods. For example, a ligand is optionally selected from amongst the chemotactic factors specified supra.

EXAMPLE 1

Operational Procedure

An example of an operational procedure is as follows:

1. Prepare a microtiter plate (any density) with positive control, negative control, unknown samples and wash solution.
2. Prepare binding agent (e.g., a protein) in stabilizing buffer at, e.g., 10 μM and add to binding agent reservoir on the microfluidic device.
3. With no flow from binding agent reservoir, sip from wash solution well until total ion current at positive control mass is stable (baseline calibration) (Refer to this as $T_1$).
4. Move capillary channel to positive control and sip until ion current at positive control mass is stable. (100% calibration, approximately 5 µM concentration assuming 50% flow into detection channel).

5. Pulse 10% binding agent into main channel for time equal to, e.g., 2× total travel time from binding agent entry point until detection point and repeat in 10% increments until 100%.
6. Observe ion current for positive control mass over this time period. Should drop to 1% of value observed in step (4). Refer to time for drop to less than 10% as $T_2$.
7. Turn off binding agent flow and move capillary channel to wash well. Sip until ion current for positive control mass returns baseline value. Refer to this as time $T_3$.
8. Move capillary channel to negative control well and sip for time $T_1$. Set mass spectrometer to monitor ion current for most intense observed mass. This mass should correspond to negative control mass.
9. Pulse protein for time $T_2$. Ion current for negative control mass should not decrease by more than 5%.
10. Turn off binding agent flow.
11. Move capillary channel to wash well and sip for time $T_3$. Ion current should return to baseline value.

EXAMPLE 2
Operational Procedure for Detecting Binding Affinities of Unknown Samples to Binding Agent An example of an operational procedure for detecting binding affinities of unknown samples (e.g., ligands) to binding agents (e.g., protein) is as follows:

A. Perform the operational procedure described above, (i.e., steps (1)–(1 1)) using positive control, negative control and wash solution to determine $T_1$, $T_2$, and $T_3$. Record the baseline value determined in step (3) and refer to this value as $V_1$.
B. Move capillary channel to well containing an unknown sample and sip for time $T_1$. Set MS to monitor ion current for most intense observed mass. Record ion current at end of $T_1$ and refer to it as $V_2$.
C. Pulse protein for time $T_2$ and record change in ion current at end of $T_2$. Refer to this value as $V_3$.
D. Turn off binding agent flow.
E. Move capillary channel to wash well and sip for time $T_3$. Record baseline ion current and refer to this value as $V_4$.
F. Repeat steps (B)–(E) for each well containing an unknown sample. At end of every row on the microtiter plate, sip from positive control and repeat steps (B)–(E).
G. If $A_{init}=B_{init}$, then calculate the approximate binding affinity of unknown samples by the equation $K_a=[A_{init}-(V_3/V_2)A_{init}]/[(V_3/V_2)A_{init}]^2$. If $A_{init}$ and $B_{init}$ are different values, the method shown in Example 3, below, is used to calculate the $K_a$.
H. Calculate the signal to noise ratio from $V_1$ and $V_2$. Calculate the confidence interval from the values $V_1$, $V_2$, and $V_3$ using the positive control at the end of each well.

EXAMPLE 3
Calculations for Bimolecular Binding Reactions

The following describes the calculation of various values, e.g., binding agent and ligand concentrations and association constants associated with the bimolecular binding interactions detected in the binding affinity assays of the present invention. For example, the concentration of a species A (e.g., a ligand) in the presence of binding agent B at equilibrium is:

$$[A]=[AB]/K_a[B]$$

Where [A], [B], and [AB] are the equilibrium concentrations of A, B and the complex AB, respectively, and $K_a$ is the association constant of A with B. If A and B are present in the same initial concentrations, $A_{init}=B_{init}$, then $$[A]=([A_{init}]-[A])/K_a[A],$$

and $$K_a(A^2)-A+A_{init}=0$$

Solving for the positive root gives $$[-1+\mathrm{sqrt}(1+4*A_{init}*K_a)]/2*K_a$$

When, e.g., $K_a=10$ µM and $A_{init}=B_{init}=10$ µM, the concentration of A at equilibrium is 6.18 µM. When $A_{init}=1$ µM, A=0.618 µM. For additional calculated values see Table 1, below. These data provide an estimate of the detection sensitivity that may be necessary for accurate approximations of binding affinities by the methods disclosed herein. Table 1. Values of $K_d$, $K_a$, and A (final concentration of detected ligand) when $A_{init}=B_{init}=1$ µM.

| $K_d$ | $K_a$ | A |
|---|---|---|
| 1ee-9 | 1ee9 | 0.031127 |
| 1ee-8 | 1ee8 | 0.095125 |
| 1ee-7 | 1ee7 | 0.270156 |
| 1ee-6 | 1ee6 | 0.618034 |
| 1ee-5 | 1ee5 | 0.91608 |
| 1ee-4 | 1ee4 | 0.990195 |
| 1ee-3 | 1ee3 | 0.999002 |

EXAMPLE 4
Experimental Procedures for Detecting Unknown Sample Binding Affinity for a Target The following includes examples of experimental procedures for detecting the binding affinity of an unknown sample (U) (e.g., a ligand) for a target (T) (e.g., a binding agent).

Device Preparation

Figure 9:
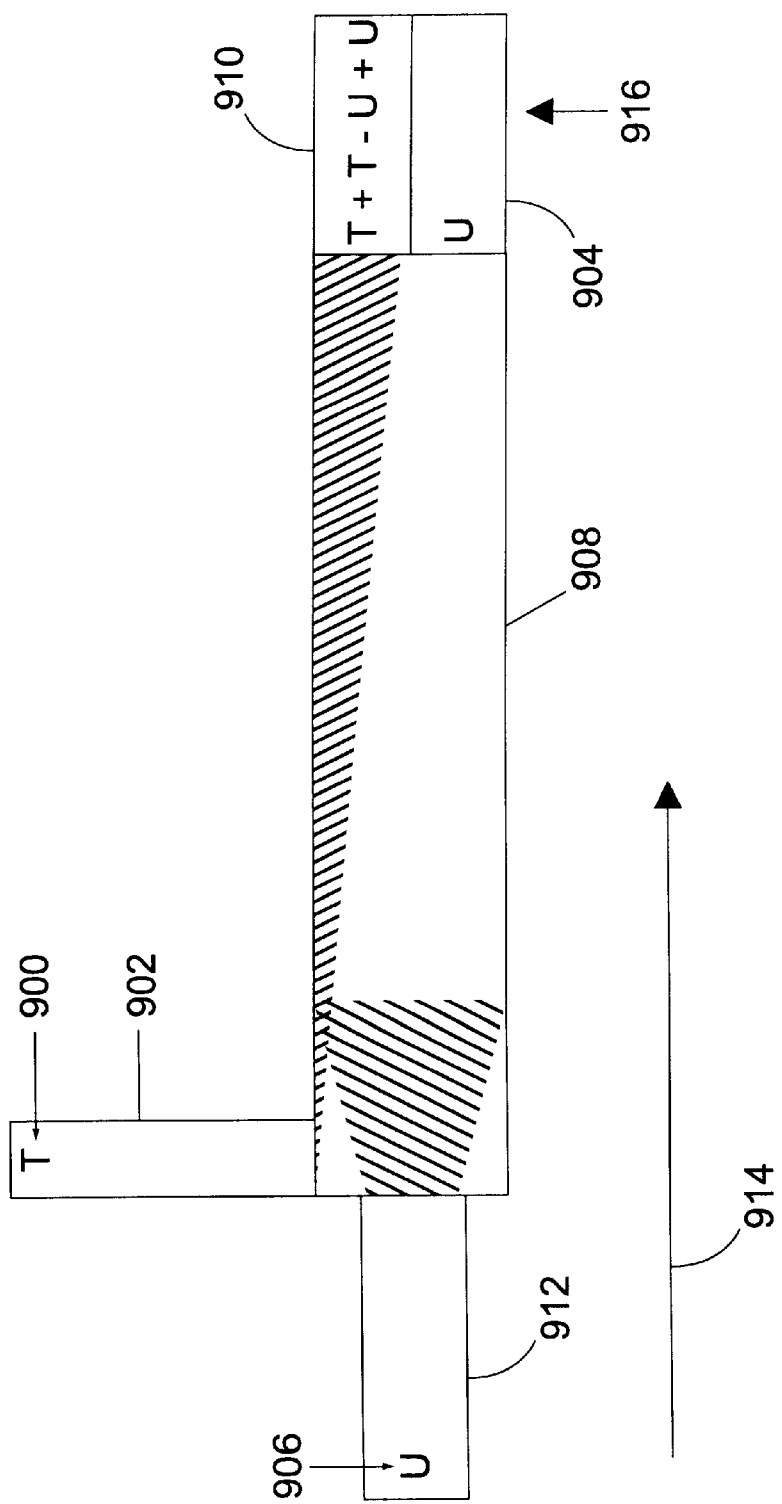
FIG. 9 illustrates a microchannel configuration for detecting binding activity.
Figure 10:
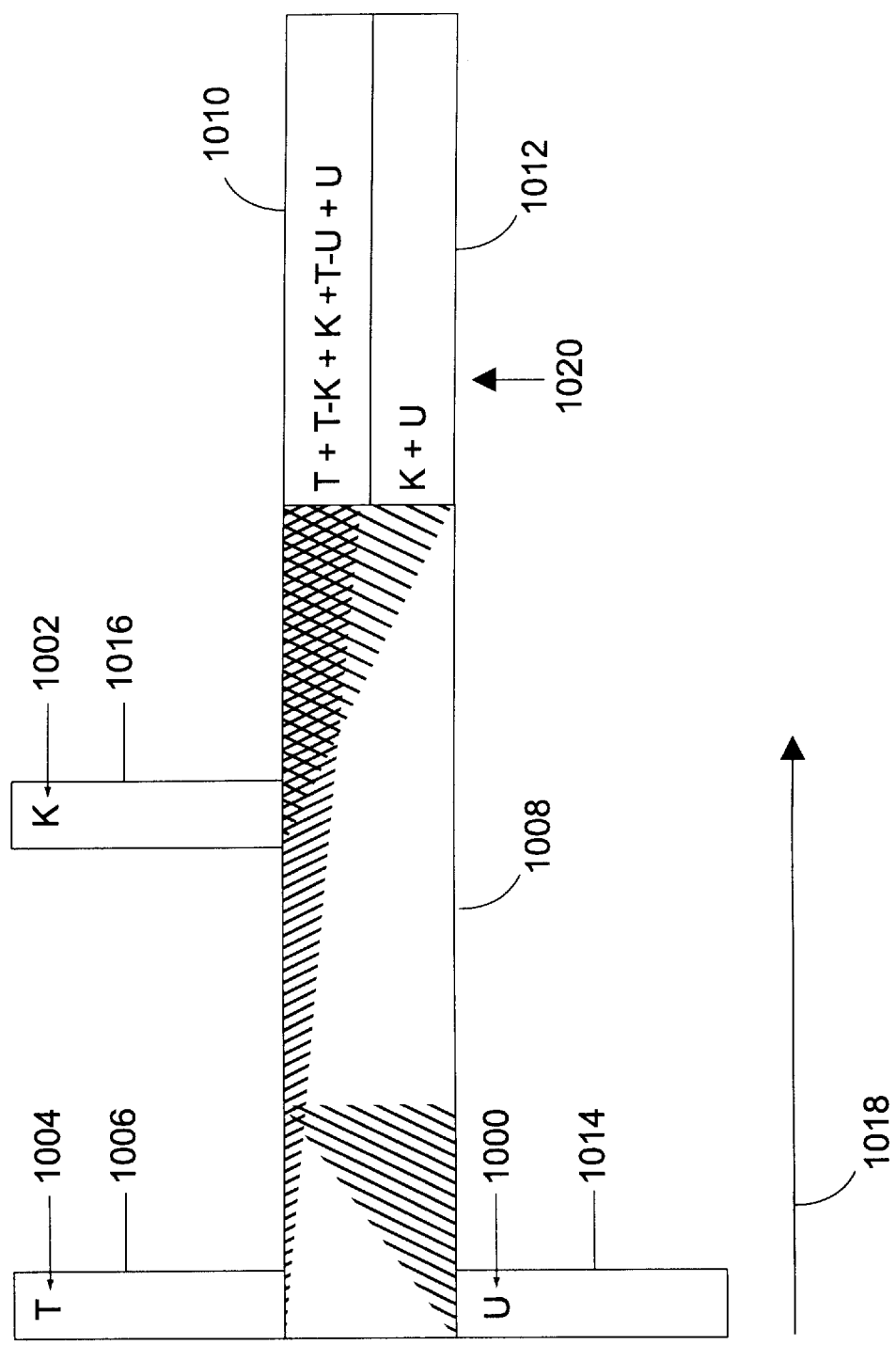
FIG. 10 illustrates a microchannel configuration for detecting competitive binding activity.

The initial step involves preparing a device such as the one depicted in FIG. 9, so that upon introduction of T 900 from target channel 902, T 900 does not substantially diffuse across main channel 908. The direction of fluid flow is indicated by arrow 914. For example, if the diffusion constant of T 900 is 5×10⁻⁷, the diffusion constant of U 906 is 5×10⁻⁵, and the flow rate is 1 mm/sec, then suitable dimensions of main channel 908 on the device are, e.g., 20 mm in length, 100 µm in width, and 100 µm in depth. Additionally, detection channel 904 (which includes detector 916 disposed proximate thereto) and binding channel 910 intersect main channel 908, as shown. In main channel 908, so configured, T 900 and any bound U 906, will diffuse on average approximately 45 µm across main channel 908 by the time they reach binding channel 910 and, in turn, will exit via binding channel 910. By comparison, unbound U 906 will diffuse across main channel 908 on average approximately 4.5 times more than T 900, and will exit via both detection channel 904 and binding channel 910. Unknown sample channel 912 optionally intersects the center of main channel 908 (as shown), as a sipper capillary which extends from the device, as a channel entering from a side of main channel 908 (as shown in FIG. 10), or any other configuration, e.g., in which T 900 exits main channel 908 substantially only from binding channel 910.

Experimental Protocol

An example experimental protocol is as follows:

(a) Prepare a multi-well microtiter plate with unknown samples in a compatible solvent such that a concentration $[U_{init}]$ (e.g., 10 μM) is introduced into the main channel.

(b) Prepare a wash well containing stabilizing buffer either on or off the microtiter plate.

(c) Place a target in stabilizing buffer in a reservoir on the chip such that a concentration $[T_{init}]$ (e.g., 10 μM) is introduced into the main channel. This concentration calculation takes into account the fact that the target does not diffuse all the way across the channel.

(d) In the absence of flow from the target reservoir, sip using, e.g., a sipper capillary from wash well until detector signal is stable (baseline calibration). A signal corresponding to approximately 0% unknown sample is observed; record this signal intensity as $V_1$. For example, a mass selective detector or an UV absorbance detector is optionally used.

(e) Move sipper capillary to an unknown sample well and sip until signal at detector is stable (e.g., at the maximum observed ion current in a mass detector, or the maximum intensity peak in a UV detector). This is the 100% calibration step. Record this signal as $V_2$.

(f) Pulse the target into the main channel for a time long enough for the target to bind to the unknown sample and to stabilize the unknown sample signal (optimally 1 to 60 seconds). Record the value of the signal at the detector as $V_3$. Optionally for higher throughput screening, the target is pulsed for just long enough to detect a detectable change in the unknown sample signal.

(g) Calculate the concentration of free (i.e., unbound) unknown [U] at the end of the main or reaction channel, as follows: $[U]=(V_3-V_1/V_2-V_1)*[U_{init}]$.

(h) Calculate the approximate concentration of free target at the end of the reaction channel, as follows: $[T]=(V_3-V_1/V_2-V_1)*[T_{init}]$.

(i) Calculate the approximate affinity constant $K_a$ of the unknown for the target using the following equation: K=[UT]/([U][T]), where [UT] is the approximate concentration of the unknown-target complex at the end of the reaction channel. Substituting the equations from steps (h) and (i) gives $K_a=([U_{init}]-[U])/[U_{init}]*([T_{init}]-[U_{init}]+[U])$.

Thus, for example if $[U_{init}]$ is 10 μM and $[T_{init}]$ is 10 μM, and the observed signals are $V_1$=2000, $V_2$=10,000, and $V_3$=6,000 units, then the calculated approximate affinity constant of U for T is $2\times10^{-5}$. A more precise $K_a$ is optionally calculated by taking several measurements using this experimental protocol at several concentrations of U and T. As a further option, many parallel channels are used with short target-unknown contact times to perform high-throughput screening of many samples simultaneously (e.g., 1 to >1,000,000 compounds). For additional discussion of parallel screening techniques, see, e.g., U.S. Pat. No. 6,046,056 to Parce, et al., entitled "High Throughput Screening Assay Systems in Microscale Fluidic Devices," which issued Apr. 4, 2000.

Competitive Binding

A related mode of detecting competitive binding activity of a ligand with a target provides another example of the uses to which the methods disclosed herein are optionally put. In cases in which a ligand that binds to the target or binding agent of interest is already known or identifiable, the diffusion-based methods described herein are optionally used to determine the affinity of an unknown compound for the target of interest by displacement of the ligand. For example, in one embodiment, the binding assay described above is initially used to identify a known ligand, and this ligand is used in the following method to quickly determine the affinity of an unknown sample for the target.

In the example below and with reference to FIG. 10, the following steps are taken to determine the ability of unknown sample 1000 to compete with known sample 1002 for binding to target 1004 (and thus the affinity of unknown sample 1000 for target 1004 at the site of binding of known sample 1002):

(1) The flow rate and the chip are of the dimensions described above (see, Device Preparation), such that:

(i) The substantially larger molecular weight target (T) 1004 enters from target sample channel 1006 and diffuses only far enough across main channel 1008 so that the majority of T 1004 exits main channel 1008 via binding channel 1010. The direction of fluid movement is indicated by arrow 1018;

(ii) The substantially smaller molecular weight unknown (U) 1000 enters main channel 1008 from unknown sample channel 1014 and diffuses rapidly across the entire main channel 1008, exiting via both detection channel 1012 (which includes detector 1020 disposed proximate thereto) and binding channel 1010. Unknown sample channel 1014 is optionally a side arm (as shown), a sipper capillary, a channel entering from the center of main channel 1008 (as shown in FIG. 9), or any other configuration that provides, e.g., adequate separation of T 1004 from U 1000; and, (iii) Known sample (K) 1002, which includes a known positive binding affinity for T 1004, enters from known sample channel 1016 and diffuses across main channel 1008 according to its diffusion constant D. The placement of known sample channel 1016 and the flow rate are chosen such that K 1002 exits via both binding channel 1010 and detection channel 1012 and with sufficient time to bind to T 1004 (optimally 1 to 60 seconds). Any diffusion constant, and therefore any molecular weight, for K 1002 is compatible with this embodiment as long as these conditions are met.

(2) A detector placed at any point along detection channel 1012 is tuned to detect the concentration of K 1002 in detection channel 1012. For example, a mass selective detector set at the molecular weight of K 1002 is optionally used.

(3) T 1004 and K 1002 are continuously flowed for a long enough period to obtain a stable signal for K 1002 at detector 1020 (optimally 1 to 60 seconds). The concentration of K 1002 observed at detector 1020 will depend on the initial concentration of K 1002, the initial concentration of T 1004, and the binding constant between the two, $K_{K-T}$.

(4) U 1000 is pulsed for a sufficient period to allow binding of U 1000 (if the unknown has a measurable binding affinity) to T 1004, and to allow the new signal for K 1002 to stabilize at detector 1020 (optimally 1 to 60 seconds).

(5) The flow of U 1000 is discontinued, and buffer is flowed along with the continuing flow of K 1002 and T 1004 until the signal for K 1002 stabilizes again.

(6) Optionally, the cycle is repeated for other unknown samples.

(7) To determine the binding constant of U 1000 for T 1004, the magnitude of the signal from Part (4) is subtracted from the magnitude of the signal from Part (3) to obtain the difference in signal (DS) in the presence and absence of target 1004. This difference in signal is proportional to the binding constant of U 1000 for T 1004 ($K_{U-T}$) provided that U 1000 competes for the same binding site on T 1004 that is occupied by K 1002.

Example of experimental conditions are as follows:

Initial main channel concentration of T=10 $\mu$M

Initial main channel concentration of K=10 $\mu$M

Initial main channel concentration of U=10 $\mu$M

Diffusion constant of target: $5\times10^{-7}$

Diffusion constant of unknown sample: $5\times10^{-5}$

Diffusion constant of known ligand $1\times10^{-6}$

Dimensions of main channel as described above (see, Device Preparation), with known sample entering 5 mm downstream of the beginning of the main channel.

A more precise $K_a$ is optionally calculated by taking several measurements, as indicated above, at several concentrations of U, K and T, and numerically solving the equation for two ligands competing for one target. As an additional option, many parallel channels are used with short target-unknown contact times to perform high-throughput screening of many samples (e.g. 1 to >1,000,000 compounds). For further discussion of parallel screening techniques, see, e.g., U.S. Pat. No. 6,046,056 to Parce, et al., entitled "High Throughput Screening Assay Systems in Microscale Fluidic Devices," which issued Apr. 4, 2000.

If there is concern that unknown U may have a substantial affinity for known K, or that the presence of U may disrupt the signal at the detector due to K, one optionally adds a step in which the signal from K is detected at the detector in the absence of T, but in the presence and absence of U. In this way the effect of U on the detection of K is optionally subtracted and thereby disregarded in calculating the affinity of U for T.

Flow of Transporters, Transmitters, Chemotactic Agents, Cells, Modulators and Other Components in Microscale Systems A variety of microscale systems which can be adapted to the present invention by incorporating transporter components, transmitter components, chemotactic agents, cells, modulators and the like are available. Microfluidic devices which can be adapted to the present invention by the addition of transporter assay components are described in various PCT applications and issued U.S. Patents by the inventors and their coworkers, including U.S. Pat. No. 5,699,157 (J. Wallace Parce) issued Dec. 16, 1997, U.S. Pat. No. 5,779,868 (J. Wallace Parce et al.) issued Jul. 14, 1998, U.S. Pat. No. 5,800,690 (Calvin Y. H. Chow et al.) issued Sep. 1, 1998, U.S. Pat. No. 5,842,787 (Anne R. Kopf-Sill et al.) issued Dec. 1, 1998, U.S. Pat. No. 5,852,495 (J. Wallace Parce) issued Dec. 22, 1998, U.S. Pat. No. 5,869,004 (J. Wallace Parce et al.) issued Feb. 9, 1999, U.S. Pat. No. 5,876,675 (Colin B. Kennedy) issued Mar. 2, 1999, U.S. Pat. No. 5,880,071 (J. Wallace Parce et al.) issued Mar. 9, 1999, U.S. Pat. No. 5,882,465 (Richard J. McReynolds) issued Mar. 16, 1999, U.S. Pat. No. 5,885,470 (J. Wallace Parce et al.) issued Mar. 23, 1999, U.S. Pat. No. 5,942,443 (J. Wallace Parce et al.) issued Aug. 24, 1999, U.S. Pat. No. 5,948,227 (Robert S. Dubrow) issued Sep. 07, 1999, U.S. Pat. No. 5,955,028 (Calvin Y. H. Chow) issued Sep. 21, 1999, U.S. Pat. No. 5,957,579 (Anne R. Kopf-Sill et al.) issued Sep. 28, 1999, U.S. Pat. No. 5,958,203 (J. Wallace Parce et al.) issued Sep. 28, 1999, U.S. Pat. No. 5,958,694 (Theo T. Nikiforov) issued Sep. 28, 1999, and U.S. Pat. No. 5,959,291 (Morten J. Jensen) issued Sep. 28, 1999; and published PCT applications, such as, WO 98/00231, WO 98/00705, WO 98/00707, WO 98/02728, WO 98/05424, WO 98/22811, WO 98/45481, WO 98/45929, WO 98/46438, and WO 98/49548, WO 98/55852, WO 98/56505, WO 98/56956, WO 99/00649, WO 99/10735, WO 99/12016, WO 99/16162, WO 99/19056, WO 99/19516, WO 99/29497, WO 99/31495, WO 99/34205, WO 99/43432, and WO 99/44217.

For example, pioneering technology providing cell based microscale assays are set forth in Parce et al. "High Throughput Screening Assay Systems in Microscale Fluidic Devices" WO 98/00231 and, e.g., in No. 60/128,643 filed Apr. 4, 1999, entitled "Manipulation of Microparticles In Microfluidic Systems," by Mehta et al. Complete integrated systems with fluid handling, signal detection, sample storage and sample accessing are available. For example, Parce et al. "High Throughput Screening Assay Systems in Microscale Fluidic Devices" WO 98/00231 provide pioneering technology for the integration of microfluidics and sample selection and manipulation.

In general, cells, modulators and other components can be flowed in a microscale system by electrokinetic (including either electroosmotic or electrophoretic) techniques, or using pressure-based flow mechanisms, or combinations thereof.

Cells in particular are desirably flowed using pressure-based flow mechanisms. Pressure forces can be applied to microscale elements to achieve fluid movement using any of a variety of techniques. Fluid flow (and flow of materials suspended or solubilized within the fluid, including cells or other particles) is optionally regulated by pressure based mechanisms such as those based upon fluid displacement, e.g., using a piston, pressure diaphragm, vacuum pump, probe or the like to displace liquid and raise or lower the pressure at a site in the microfluidic system. The pressure is optionally pneumatic, e.g., a pressurized gas, or uses hydraulic forces, e.g., pressurized liquid, or alternatively, uses a positive displacement mechanism, i.e., a plunger fitted into a material reservoir, for forcing material through a channel or other conduit, or is a combination of such forces.

In other embodiments, a vacuum source is applied to a reservoir or well at one end of a channel to draw the suspension through the channel. Pressure or vacuum sources are optionally supplied external to the device or system, e.g., external vacuum or pressure pumps sealably fitted to the inlet or outlet of the channel, or they are internal to the device, e.g., microfabricated pumps integrated into the device and operably linked to the channel. Examples of microfabricated pumps have been widely described in the art. See, e.g., published International Application No. WO 97/02357.

Hydrostatic, wicking and capillary forces can also be used to provide pressure for fluid flow of materials such as cells. See, e.g., "METHOD AND APPARATUS FOR CONTINUOUS LIQUID FLOW IN MICROSCALE CHANNELS USING PRESSURE INJECTION, WICKING AND ELECTROKINETIC INJECTION," by Alajoki et al., U.S. Ser. No. 09/245,627, filed Feb. 5, 1999. In these methods, an adsorbent material or branched capillary structure is placed in fluidic contact with a region where pressure is applied, thereby causing fluid to move towards the adsorbent material or branched capillary structure.

Mechanisms for reducing adsorption of materials during fluid-based flow are described in "PREVENTION OF SURFACE ADSORPTION IN MICROCHANNELS BY APPLICATION OF ELECTRIC CURRENT DURING PRESSURE-INDUCED FLOW" filed May 11, 1999 by Parce et al., Ser. No. 09/310,027. In brief, adsorption of cells, transmitters, chemotactic factors, potential modulators and other materials to channel walls or other microscale components during pressure-based flow can be reduced by applying an electric field such as an alternating current to the material during flow.

Mechanisms for focusing cells and other components into the center of microscale flow paths, which is useful in increasing assay throughput by regularizing flow velocity is described in "FOCUSING OF MICROPARTICLES IN MICROFLUIDIC SYSTEMS" by H. Garrett Wada et al. Ser. No. 60/134,472, filed May 17, 1999. In brief, cells are focused into the center of a channel by forcing fluid flow from opposing side channels into the main channel comprising the cells, or by other fluid manipulations. Diffusible materials such as the transmitters of the present invention are also optionally washed from cells as described by Wada et al. during flow of the cells, i.e., by sequentially flowing buffer into a channel in which cells are flowed and flowing the buffer back out of the channel.

In an alternate embodiment, microfluidic systems can be incorporated into centrifuge rotor devices, which are spun in a centrifuge. Fluids and particles travel through the device due to gravitational and centripetal/centrifugal pressure forces.

One method of achieving transport or movement of transmitters, chemotactic factors, enzymes, receptors, ligands, modulators, and even cells (particularly transmitters and modulators) through microfluidic channels is by electrokinetic material transport. "Electrokinetic material transport systems," as used herein, include systems that transport and direct materials within a microchannel and/or chamber containing structure, through the application of electrical fields to the materials, thereby causing material movement through and among the channel and/or chambers, i.e., cations will move toward a negative electrode, while anions will move toward a positive electrode. For example, movement of fluids toward or away from a cathode or anode can cause movement of transmitters, cells, chemotactic factors, enzymes, receptors, ligands, modulators, etc. suspended within the fluid. Similarly, the transmitters, cells, chemotactic factors, enzymes, receptors, ligands, modulators, etc. can be charged, in which case they will move toward an oppositely charged electrode (indeed, in this case, it is possible to achieve fluid flow in one direction while achieving particle flow in the opposite direction). In this embodiment, the fluid can be immobile or flowing and can comprise a matrix as in electrophoresis.

In general, electrokinetic material transport and direction systems also include those systems that rely upon the electrophoretic mobility of charged species within the electric field applied to the structure. Such systems are more particularly referred to as electrophoretic material transport systems. For electrophoretic applications, the walls of interior channels of the electrokinetic transport system are optionally charged or uncharged. Typical electrokinetic transport systems are made of glass, charged polymers, and uncharged polymers. The interior channels are optionally coated with a material which alters the surface charge of the channel.

A variety of electrokinetic controllers and systems are described, e.g., in Ramsey WO 96/04547, Parce et al. WO 98/46438 and Dubrow et al., WO 98/49548, as well as a variety of other references noted herein.

Use of electrokinetic transport to control material movement in interconnected channel structures was described, e.g., in WO 96/04547 and U.S. Pat. No. 5,858,195 to Ramsey. An exemplary controller is described in U.S. Pat. No. 5,800,690. Modulating voltages are concomitantly applied to the various reservoirs to affect a desired fluid flow characteristic, e.g., continuous or discontinuous (e.g., a regularly pulsed field causing the sample to oscillate direction of travel) flow of labeled components toward a waste reservoir. Particularly, modulation of the voltages applied at the various reservoirs can move and direct fluid flow through the interconnected channel structure of the device.

Sources of Assay Components and Integration with Microfluidic Formats

Sources of transporter containing components such as cells or cell fractions, sources of transmitters, adhesion factors, chemotactic factors, enzymes, receptors, ligands, and sources of components such as cells or cell fractions comprising transmitter receptors can be fluidly coupled to the microchannels noted herein in any of a variety of ways. In particular, those systems comprising sources of materials set forth in Knapp et al. "Closed Loop Biochemical Analyzers" (WO 98/45481; PCT/US98/06723) and Parce et al. "High Throughput Screening Assay Systems in Microscale Fluidic Devices" WO 98/00231 and, e.g., in No. 60/128,643 filed Apr. 4, 1999, entitled "Manipulation of Microparticles In Microfluidic Systems," by Mehta et al. are applicable.

In these systems, a "pipettor channel" (a channel in which components can be moved from a source to a microscale element such as a second channel or reservoir) is temporarily or permanently coupled to a source of material. The source can be internal or external to a microfluidic device comprising the pipettor channel. Example sources include microwell plates, membranes or other solid substrates comprising lyophilized components, wells or reservoirs in the body of the microscale device itself and others.

For example, the source of a cell type, component, or modulator reagent can be a microwell plate external to the body structure, having, e.g., at least one well with the selected cell type or reagent. Alternatively, a well disposed on the surface of the body structure comprising the selected cell type, component, or reagent, a reservoir disposed within the body structure comprising the selected cell type, component or reagent; a container external to the body structure comprising at least one compartment comprising the selected particle type or reagent, or a solid phase structure comprising the selected cell type or reagent in lyophilized or otherwise dried form.

Figure 2:
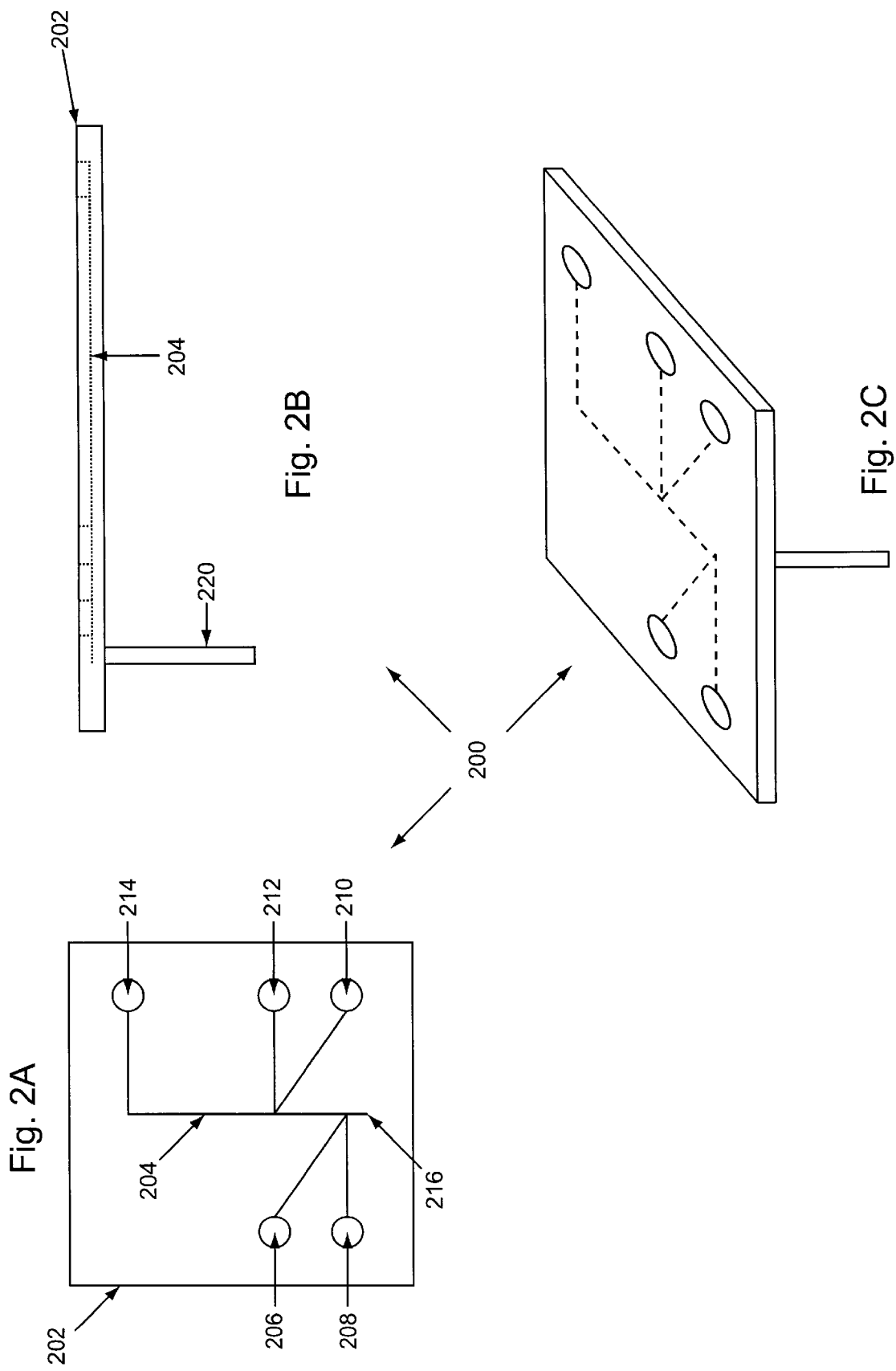
FIG. 2, panels A, B and C are schematic drawings of an integrated system of the invention, including a body structure, microfabricated elements, and a pipettor channel.
Figure 3:
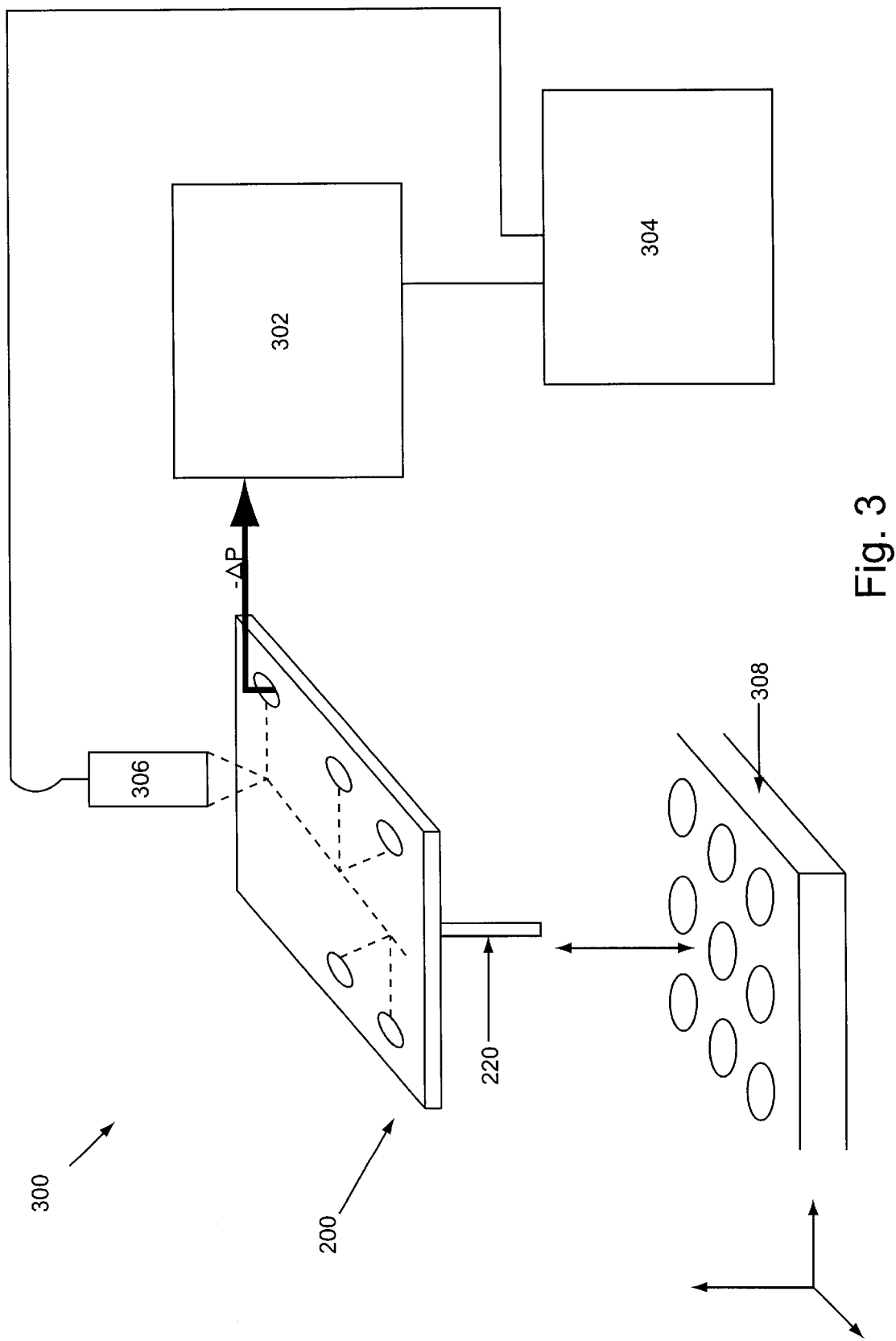
FIG. 3 is a schematic drawing of the integrated system of FIG. 2, further depicting incorporation of a microwell plate, a computer, a detector and a voltage/pressure controller.

A loading channel region is optionally fluidly coupled to a pipettor channel with a port external to the body structure, e.g., as depicted in FIGS. 2 and 3. The loading channel can be coupled to an electropipettor channel with a port external to the body structure, a pressure-based pipettor channel with a port external to the body structure, a pipettor channel with a port internal to the body structure, an internal channel within the body structure fluidly coupled to a well on the surface of the body structure, an internal channel within the body structure fluidly coupled to a well within the body structure, or the like. Example configurations are depicted in the figures herein.

As described more fully herein, the integrated microfluidic system of the invention can include a very wide variety of storage elements for storing reagents to be assessed. These include well plates, matrices, membranes and the like. The reagents are stored in liquids (e.g., in a well on a microtiter plate), or in lyophilized form (e.g., dried on a membrane or in a porous matrix), and can be transported to an array component of the microfluidic device using conventional robotics, or using an electropipettor or pressure pipettor channel fluidly coupled to a reaction or reagent channel of the microfluidic system.

In general, the test modulator compounds are separately introduced into the assay systems described herein, or at least introduced in relatively manageable pools of modulator materials. The relative level of a particular cellular transport function is then assessed in the presence of the test compound, and this relative level of function is then compared to a control system, which lacks an introduced test modulator compound. Increases or decreases in relative cellular function are indicative that the test compound is an enhancer or an inhibitor of the particular cellular function, respectively.

Detectors and Integrated Systems

Although the devices and systems specifically illustrated herein are generally described in terms of the performance of a few or one particular operation, it will be readily appreciated from this disclosure that the flexibility of these systems permits easy integration of additional operations into these devices. For example, the devices and systems described will optionally include structures, reagents and systems for performing virtually any number of operations both upstream and downstream from the operations specifically described herein. Such upstream operations include sample handling and preparation operations, e.g., cell separation, extraction, purification, amplification, cellular activation, labeling reactions, dilution, aliquotting, and the like. Similarly, downstream operations may include similar operations, including, e.g., separation of sample components, labeling of components, assays and detection operations, electrokinetic or pressure-based injection of components into contact with particle sets, or materials released from particle sets, or the like.

Assay and detection operations include, without limitation, cell fluorescence assays, cell activity assays, probe interrogation assays, e.g., nucleic acid hybridization assays utilizing individual probes, free or tethered within the channels or chambers of the device and/or probe arrays having large numbers of different, discretely positioned probes, receptor/ligand assays, immunoassays, and the like. Any of these elements can be fixed to array members, or fixed, e.g., to channel walls, or the like.

Instrumentation

In the present invention, the materials such as cells are optionally monitored and/or detected so that an activity can be determined. Depending on the label signal measurements, decisions are can be made regarding subsequent fluidic operations, e.g., whether to assay a particular modulator in detail to determine kinetic information.

The systems described herein generally include microfluidic devices, as described above, in conjunction with additional instrumentation for controlling fluid transport, flow rate and direction within the devices, detection instrumentation for detecting or sensing results of the operations performed by the system, processors, e.g., computers, for instructing the controlling instrumentation in accordance with preprogrammed instructions, receiving data from the detection instrumentation, and for analyzing, storing and interpreting the data, and providing the data and interpretations in a readily accessible reporting format.

Controllers

A variety of controlling instrumentation is optionally utilized in conjunction with the microfluidic devices described above, for controlling the transport and direction of fluids and/or materials within the devices of the present invention, e.g., by pressure-based or electrokinetic control.

For example, in many cases, fluid transport and direction are controlled in whole or in part, using pressure based flow systems that incorporate external or internal pressure sources to drive fluid flow. Internal sources include microfabricated pumps, e.g., diaphragm pumps, thermal pumps, lamb wave pumps and the like that have been described in the art. See, e.g., U.S. Pat. Nos. 5,271,724, 5,277,556, and 5,375,979 and Published PCT Application Nos. WO 94/05414 and WO 97/02357. As noted above, the systems described herein can also utilize electrokinetic material direction and transport systems. Preferably, external pressure sources are used, and applied to ports at channel termini. These applied pressures, or vacuums, generate pressure differentials across the lengths of channels to drive fluid flow through them. In the interconnected channel networks described herein, differential flow rates on volumes are optionally accomplished by applying different pressures or vacuums at multiple ports, or preferably, by applying a single vacuum at a common waste port and configuring the various channels with appropriate resistance to yield desired flow rates. Example systems are described in U.S. Ser. No. 09/238,467 filed Jan. 28, 1999.

Typically, the controller systems are appropriately configured to receive or interface with a microfluidic device or system element as described herein. For example, the controller and/or detector, optionally includes a stage upon which the device of the invention is mounted to facilitate appropriate interfacing between the controller and/or detector and the device. Typically, the stage includes an appropriate mounting/alignment structural element, such as a nesting well, alignment pins and/or holes, asymmetric edge structures (to facilitate proper device alignment), and the like. Many such configurations are described in the references cited herein.

The controlling instrumentation discussed above is also used to provide for electrokinetic injection or withdrawal of material downstream of the region of interest to control an upstream flow rate. The same instrumentation and techniques described above are also utilized to inject a fluid into a downstream port to function as a flow control element.

Detector

The devices herein optionally include signal detectors, e.g., which detect fluorescence, phosphorescence, radioactivity, pH, charge, absorbance, refractive index, luminescence, temperature, magnetism or the like. Fluorescent detection is preferred.

More specifically, the detectors used in the devices and systems of the present invention can include, e.g. an optical detector, a microscope, a CCD array, a photomultiplier tube, a photodiode, an emission spectroscope, a fluorescence spectroscope, a phosphorescence spectroscope, a luminescence spectroscope, a spectrophotometer, a photometer, a nuclear magnetic resonance spectrometer, an electron paramagnetic resonance spectrometer, an electron spin resonance spectroscope, a turbidimeter, a nephelometer, a Raman spectroscope, a refractometer, an interferometer, an x-ray diffraction analyzer, an electron diffraction analyzer, a polarimeter, an optical rotary dispersion analyzer, a circular dichroism spectrometer, a potentiometer, a chronopotentiometer, a coulometer, an amperometer, a conductometer, a gravimeter, a mass spectrometer, a thermal gravimeter, a titrimeter, a differential scanning colorimeter, a radioactive activation analyzer, a radioactive isotopic dilution analyzer, and the like. Especially preferred detectors for use in the methods and devices of the invention include optical detectors and, e.g., electrospray ionization mass spectrometers, which can, e.g., be proximal to or coupled to one or more microscale channels of a device. Detector embodiments including mass spectrometer elements are discussed further below.

The detector(s) optionally monitors one or a plurality of signals from upstream and/or downstream of an assay mixing point in which, e.g., a ligand and an enzyme or a receptor, or a transmitter and a cell or other component with a transmitter receptor and the cell or other component with transporter activity are mixed. For example, the detector can monitor a plurality of optical signals which correspond in position to "real time" assay results.

Example detectors include photomultiplier tubes, a CCD array, a scanning detector, a galvo-scann or the like. Cells or other components which emit a detectable signal can be flowed past the detector, or, alternatively, the detector can move relative to the array to determine cell position (or, the detector can simultaneously monitor a number of spatial positions corresponding to channel regions, e.g., as in a CCD array).

The detector can include or be operably linked to a computer, e.g., which has software for converting detector signal information into assay result information (e.g., kinetic data of modulator activity), or the like.

Signals from arrays are optionally calibrated, e.g., by calibrating the microfluidic system by monitoring a signal from a known source.

A microfluidic system can also employ multiple different detection systems for monitoring the output of the system. Detection systems of the present invention are used to detect and monitor the materials in a particular channel region (or other reaction detection region). Once detected, the flow rate and velocity of cells in the channels is also optionally measured and controlled as described above. As described in PCT/US98/11969, correction of kinetic information based upon flow velocity can be used to provide accurate kinetic information.

Examples of detection systems include optical sensors, temperature sensors, pressure sensors, pH sensors, conductivity sensors, mass sensors, and the like. Each of these types of sensors is readily incorporated into the microfluidic systems described herein. In these systems, such detectors are placed either within or adjacent to the microfluidic device or one or more channels, chambers or conduits of the device, such that the detector is within sensory communication with the device, channel, or chamber. The phrase "within sensory communication" of a particular region or element, as used herein, generally refers to the placement of the detector in a position such that the detector is capable of detecting the property of the microfluidic device, a portion of the microfluidic device, or the contents of a portion of the microfluidic device, for which that detector was intended. For example, a pH sensor placed in sensory communication with a microscale channel is capable of determining the pH of a fluid disposed in that channel. Similarly, a temperature sensor placed in sensory communication with the body of a microfluidic device is capable of determining the temperature of the device itself.

Particularly preferred detection systems include optical detection systems for detecting an optical property of a material within the channels and/or chambers of the microfluidic devices that are incorporated into the microfluidic systems described herein. Such optical detection systems are typically placed adjacent to a microscale channel of a microfluidic device, and are in sensory communication with the channel via an optical detection window that is disposed across the channel or chamber of the device. Optical detection systems include systems that are capable of measuring the light emitted from material within the channel, the transmissivity or absorbance of the material, as well as the materials spectral characteristics. In preferred aspects, the detector measures an amount of light emitted from the material, such as a fluorescent or chemiluminescent material. As such, the detection system will typically include collection optics for gathering a light based signal transmitted through the detection window, and transmitting that signal to an appropriate light detector. Microscope objectives of varying power, field diameter, and focal length are readily utilized as at least a portion of this optical train. The light detectors are optionally photodiodes, avalanche photodiodes, photomultiplier tubes, diode arrays, or in some cases, imaging systems, such as charged coupled devices (CCDs) and the like. In preferred aspects, photodiodes are utilized, at least in part, as the light detectors. The detection system is typically coupled to a computer (described in greater detail below), via an analog to digital or digital to analog converter, for transmitting detected light data to the computer for analysis, storage and data manipulation.

In the case of fluorescent materials such as labeled cells, the detector typically includes a light source which produces light at an appropriate wavelength for activating the fluorescent material, as well as optics for directing the light source through the detection window to the material contained in the channel or chamber. The light source can be any number of light sources that provides an appropriate wavelength, including lasers, laser diodes and LEDs. Other light sources required for other detection systems. For example, broad band light sources are typically used in light scattering/transmissivity detection schemes, and the like. Typically, light selection parameters are well known to those of skill in the art.

The detector can exist as a separate unit, but is preferably integrated with the controller system, into a single instrument. Integration of these functions into a single unit facilitates connection of these instruments with the computer (described below), by permitting the use of few or a single communication port(s) for transmitting information between the controller, the detector and the computer.

Mass Spectrometry

Mass spectrometry is a widely used analytical technique that can be used to provide information about, e.g., the isotopic ratios of atoms in samples, the structures of various molecules, including biologically important molecules (e.g., transporter molecules, transmitters, enzymes, receptors, chemotactic factors, and the like), and the qualitative and quantitative composition of complex mixtures. Common mass spectrometer systems include a system inlet, an ion source, a mass analyzer, and a detector which are under vacuum. The detector is typically operably connected to a signal processor and a computer. Desorption ion sources for use in the present invention, include field desorption (FD), electrospray ionization (ESI), chemical ionization, matrix-assisted desorption/ionization (MALDI), plasma desorption (PD), fast atom bombardment (FAB), secondary ion mass spectrometry (SIMS), and thermospray ionization (TS). As mentioned, ESI sources are especially preferred.

Mass spectrometry is well-known in the art. References specifically addressing the interfacing of mass spectrometers with microfluidic devices include, e.g., Karger, et al., U.S. Pat. No. 5,571,398, "PRECISE CAPILLARY ELECTROPHORETIC INTERFACE FOR SAMPLE COLLECTION OR ANALYSIS" and Karger, et al. U.S. Pat. No. 5,872,010

"MICROSCALE FLUID HANDLING SYSTEM." General sources of information about mass spectrometry include, e.g., Skoog, et al. *Principles of Instrumental Analysis* ($5^{th}$ Ed.) Hardcourt Brace & Company, Orlando (1998). In general, mass spectrometers are well suited to interface with microfluidic devices, because the usual input into a microfluidic system is a capillary channel. In the present invention, this mass spectrometry capillary is simply fluidly coupled to channel in the microscale system. Methods of affixing external capillaries to microscale systems include various bonding and/or drilling operations, as described, e.g., in Parce, et al., U.S. Pat. No. 5,972,187 "ELECTROPIPETTOR AND COMPENSATION MEANS FOR ELECTROPHORETIC BIAS." One particular advantage of coupling mass spectrometers to microfluidic systems is that the ionization chamber of a mass spectrometer is usually under vacuum. This vacuum can be used as a negative pressure source for the microfluidic system, providing a driving mechanism for the system.

Figure 7:
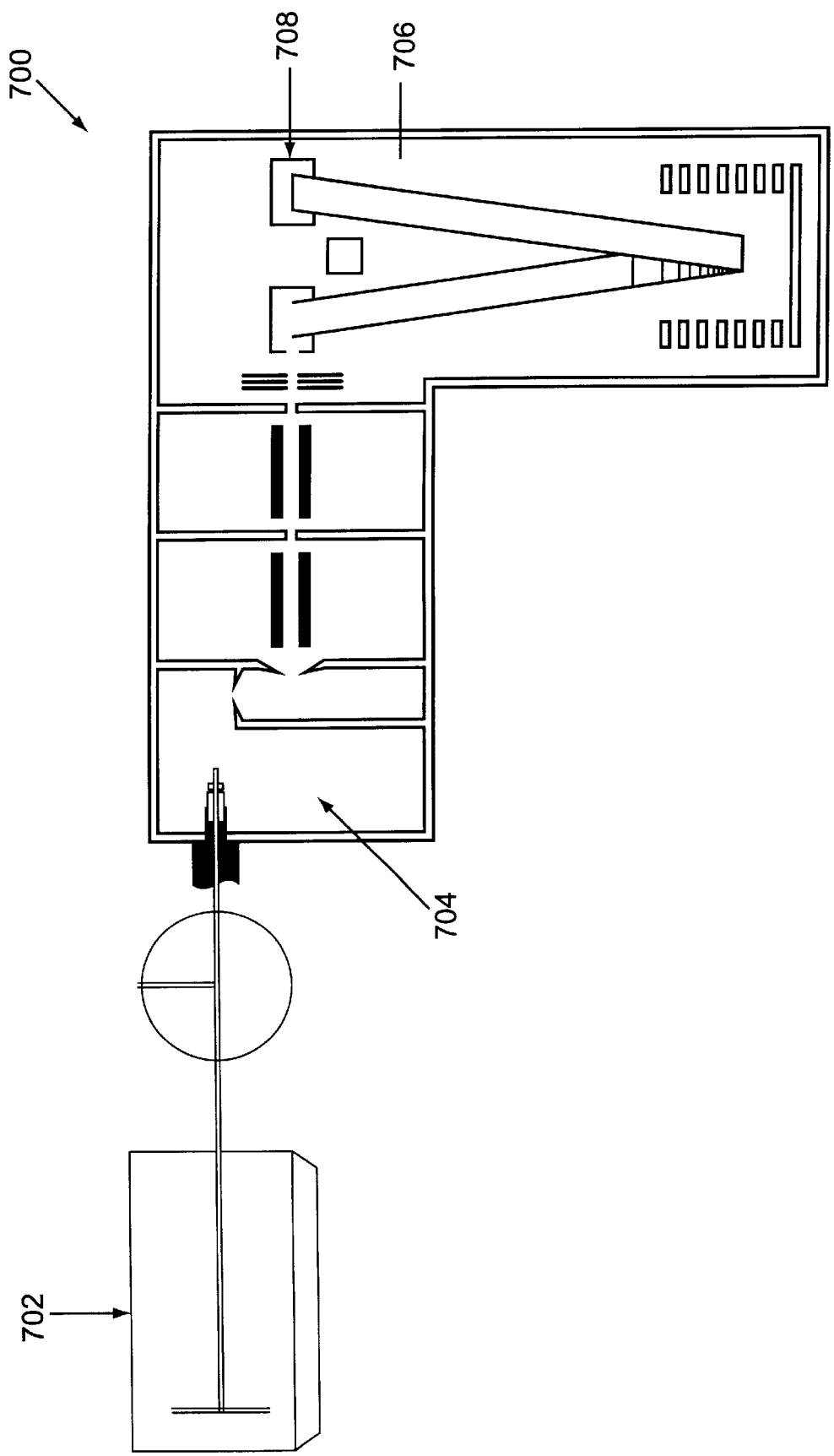
FIG. 7 is a schematic showing an interface between a microfluidic device and electrospray ionization mass spectrometer.

FIG. 7 is a schematic of an interface between a microfluidic device and an ESI mass spectrometer. The interfaced system 700 is optionally used, e.g., to identify and/or determine the concentration of various molecules (e.g., drug-like organic molecules) in the effluent in one or more microchannels. Such effluent is typically drawn from device 702 into ion source 704 using the negative pressure of ion source 704. A shown, time of flight (TOF) mass analyzer 706 with detector 708 is included in this system. In the systems of the present invention, the molecular weights of samples to be analyzed can be in the range of from about 150 Kd to about 800 Kd, e.g., about 500 Kd. Effluent concentrations can be, e.g., in the range of about 1 $\mu$M to about 10 $\mu$M, e.g., about 5 $\mu$M.

Computer

As noted above, either or both of the controller system and/or the detection system are coupled to an appropriately programmed processor or computer which functions to instruct the operation of these instruments in accordance with preprogrammed or user input instructions, receive data and information from these instruments, and interpret, manipulate and report this information to the user. As such, the computer is typically appropriately coupled to one or both of these instruments (e.g., including an analog to digital or digital to analog converter as needed).

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation. The computer then receives the data from the one or more sensors/detectors included within the system, and interprets the data, either provides it in a user understood format, or uses that data to initiate further controller instructions, in accordance with the programming, e.g., such as in monitoring and control of flow rates, temperatures, applied voltages, and the like.

In the present invention, the computer typically includes software for the monitoring of materials in the channels. Additionally the software is optionally used to control electrokinetic or pressure modulated injection or withdrawal of material. The injection or withdrawal is used to modulate the flow rate as described above.

Example System

FIG. 2, panels A, B and C and FIG. 3 provide additional details regarding example integrated systems of the invention. As shown, body structure 202 has main channel 204 fabricated therein. Cells with transporter activity are flowed from reservoir 214, e.g., by applying a vacuum at vacuum source 216 (and/or at any of the reservoirs or wells noted below) through main channel 204. Cells with transmitter receptor, or transmitter, or a potential modulator or a different material such as a buffer or label can be flowed from wells 210 or 212 and into main channel 204. Cells with transmitter receptor, or transmitter, or a potential modulator or any additional material can be flowed from wells 206 or 208, or materials can be flowed into these wells, e.g., when they are used as waste wells, or when they are coupled to a vacuum source. Flow from wells 214, 212, 210, 206, or 208 can be performed by modulating fluid pressure, or by electrokinetic approaches as described. Instead of the arrangement of channels depicted in FIG. 2, an arrangement with opposing channels, as depicted in FIG. 1 can be substituted.

Transmitter, transporters, or material with transmitter receptors can be flowed from the enumerated wells, or can be flowed from a source external to body 202. As depicted, the integrated system can include pipettor channel 220, e.g., protruding from body 202, for accessing an outside source of reagents. For example, as further depicted in system 300 as shown in FIG. 3, pipettor channel 220 can access microwell plate 308 which includes cells, transmitters, transporters, activity modulators, controls, or the like, in the wells of the plate. For example, a library of potential inhibitor compounds can be stored in the wells of plate 308 for easy access by the system. Inhibitors or other reagents relevant to the assays can be flowed into channel 204 through pipettor channel 220. Detector 306 is in sensory communication with channel 204, detecting signals resulting, e.g., from the interaction of a transmitter with a transmitter receptor, as described above. Detector 306 is operably linked to Computer 304, which digitizes, stores and manipulates signal information detected by detector 306. Voltage/pressure controller 302 controls voltage, pressure, or both, e.g., at the wells of the system, or at vacuum couplings fluidly coupled to channel 204 (or the other channels noted above). Optionally, as depicted, computer 304 controls voltage/pressure controller 302. In one set of embodiments, computer 304 uses signal information to select further reaction parameters. For example, upon detecting transporter inhibition by a potential modulator in a well from plate 308, the computer optionally directs withdrawal of additional aliquots of the potential modulator through pipettor channel 220, e.g., to deliver different concentrations of the potential modulator to the assay, e.g., to determine kinetic data (such as a dose-response curve) for the potential modulator.

Kits

Generally, the microfluidic devices described herein are optionally packaged to include reagents for performing the device's preferred function. For example, the kits can include any of microfluidic devices described along with assay components, reagents, sample materials, control materials, or the like. Such kits also typically include appropriate instructions for using the devices and reagents, and in cases where reagents are not predisposed in the devices themselves, with appropriate instructions for introducing the reagents into the channels and/or chambers of the device. In this latter case, these kits optionally include special ancillary devices for introducing materials into the microfluidic systems, e.g., appropriately configured syringes/pumps, or the like (in one preferred embodiment, the device itself comprises a pipettor element, such as an electropipettor for introducing material into channels and chambers within the device). In the former case, such kits typically include a microfluidic device with necessary reagents predisposed in the channels/chambers of the device. Generally, such reagents are provided in a stabilized form, so as to prevent degradation or other loss during prolonged storage, e.g., from leakage. A number of stabilizing processes are widely used for reagents that are to be stored, such as the inclusion of chemical stabilizers (i.e., enzymatic inhibitors, microcides/bacteriostats, anticoagulants), the physical stabilization of the material, e.g., through immobilization on a solid support, entrapment in a matrix (i.e., a gel), lyophilization, or the like.

The kits of the present invention can optionally include a first, second, and third component. The first component, e.g., an adhesion factor, can include a first attachment activity. The second component, e.g., a motile cell, can include a second attachment activity and be capable of detaching from the first component in response to the third component, e.g., a chemotactic factor, that is capable of forming a gradient. These kits can also include a container for packaging the at least one first, second, and third components, instructions for practicing the methods herein, reagents for buffering or storing the at least one first, second, and third components, and/or one or more test compounds.

A kit can optionally include a first component (e.g., an enzyme or receptor) or a set of first components and a second component (e.g., a ligand) or a set of second components, in which the first component or the set of first components can diffuse more rapidly in solution than the second component or the set of second components. The first component or the set thereof can substantially diffuse across a channel in a mixing longitudinal segment when the first and second components or the sets thereof are concomitantly flowed in the channel. However, the second component or the set thereof typically diffuse less than substantially across the first channel in the mixing longitudinal segment. Furthermore, the second component or the set thereof can bind to the first component or the set of first components. The kit can also include a container for packaging the first and second components or the sets thereof, instructions for practicing the method herein, reagents for buffering or storing the at least one first and second components or the sets thereof, and one or more test compounds.

Kits also optionally include packaging materials or containers for holding microfluidic device, system or reagent elements.

The discussion above is generally applicable to the aspects and embodiments of the invention described in the claims.

Moreover, modifications can be made to the method and apparatus described herein without departing from the spirit and scope of the invention as claimed, and the invention can be put to a number of different uses including the following:

The use of a microfluidic system for performing the transporter, gradient, and binding assays set forth herein.

The use of a microfluidic system as described herein, wherein a biochemical system flows through one of said channels substantially continuously, providing for, e.g., sequential testing of a plurality of transporter or ligand compounds.

The use of electrokinetic injection in a microfluidic device as described herein to modulate or achieve flow of transporters, transmitters or other assay components in channels of a microscale device, optionally in conjunction with pressure-based flow mechanisms.

The optional use of a combination of adsorbent materials, electrokinetic injection and pressure based flow elements in a microfluidic device as described herein to modulate or achieve flow of materials e.g., in the channels of the device.

An assay utilizing a use of any one of the microfluidic systems or substrates described herein.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patent documents, and other references cited in this application are incorporated by reference in their entirety for all purposes to the same extent as if each individual publication or patent document were individually so denoted.

What is claimed is:

1. A method of determining an effect of a compound on a transporter activity of a component, the method comprising:

concomitanly flowing through a first channel a first component comprising the transporter activity, a transportable molecule that interacts with said first component, and a second component comprising a receptor to said transportable molecule that competitively binds with the transportable molecule;

detecting a first signal produced by competitive binding of the receptor to the transportable molecule;

concomitantly flowing through the first channel the first component, the transportable molecule, the second component, and a third component;

detecting a second signal produced by the competitive binding of the receptor to the transportable molecule in the presence of the third component; and comparing the first and second signals to determine the effects of the third component on the transporter activity of the first component.

2. The method of claim 1, the method comprising sequentially flowing the first and second components in the first channel.

3. The method of claim 2, wherein the first component is a cell comprising transporter activity and the second component is a cell comprising a receptor for the transportable molecule.

4. The method of claim 1, comprising flowing the first component, the second component, and the transportable molecule in the absence of the third component, thereby serving as a positive control for the signal produced by contacting the third component with the transportable molecule.

5. The method of claim 1, wherein the first or second components comprise a carrier moiety or set of carrier moieties, the carrier or carrier set comprising a receptor or transporter, the carrier set comprising one or more of: a cell, a liposome, an organelle, a protein, and a protein-lipid complex.

6. The method of claim 1, wherein the transportable molecule or set of transportable molecules is selected from one or more of: a neurotransmitter, a set of neurotransmitters, a protein, a set of proteins, a peptide, a set of peptides, a lipid, a set of lipids, a carbohydrate, a set of carbohydrates, an organic molecule, a set of organic molecules, a drug, a set of drugs, a receptor ligand, a set of receptor ligands, an antibody, a set of antibodies, a cytokine, a set of cytokines, a chemokine, a set of chemokines, a hormone, and a set of hormones.

7. The method of claim 1, wherein the first component is a carrier moiety or set of carrier moieties comprising transporter activity, the transporter activity selected from: a monoamine transporter, a betaine transporter, a creatine transporter, a gamma-aminobutyric acid transporter, a glycine transporter, a proline transporter and a taurine transporter.

8. The method of claim 1, wherein the transportable molecule is selected from acetylcholine, a catecholamine, epinephrine, norepinephrine, dopamine, serotonin, an adrenergic neurotransmitter, an endorphin, $\alpha$-endorphin, $\beta$-endorphin, an enkephalin, Met-enkephalin, Leu-enkphalin, somatostatin, leutinizing hormone-releasing hormone, thyrotropin-releasing hormone, substance P, angiotensin I, angiotensin II, vasoactive intestinal peptide, serotonin, and gamma-aminobutyric acid (GABA).

9. The method of claim 1, the method comprising flowing the transportable molecule from a second channel into the first channel and flowing the second component from a third channel into the first channel, whereby the first component, the second component and the transportable molecule mix in the first channel.

10. The method of claim 1, the method comprising:
   flowing the transportable molecule into the first channel from a second channel, and
   flowing the second component into the first channel from a third channel;
   wherein the second and third channels intersect the first channel in a mixing region, wherein the first, second and third components diffuse into contact in the mixing region.

11. The method of claim 1, the method comprising concomitantly flowing the transportable molecule and the second component into the first channel.

12. The method of claim 1, wherein the first component, the second component, the third component, and the transportable molecule are flowed using one or more fluid direction component comprising one or more of: a fluid pressure force modulator, an electrokinetic force modulator, a capillary force modulator and a fluid wicking element.

13. The method of claim 1, wherein the first channel is a microchannel.

14. The method of claim 1, wherein the concentration of the transportable molecule is decreased in solution in the first channel as the first component internalizes the transportable molecule.

15. The method of claim 1, wherein the detectable signal is selected from: a cellular activity, a light emission, a radioactive emission, a change in pH and a change in temperature.

16. The method of claim 1, further comprising varying the concentration of one or more of: the first component, the transportable molecule, the third component, and the second component in the first channel and measuring the resulting increase or decrease in signal strength.

17. A kit comprising a first and second component, the first component comprising a transporter activity and the second component being capable of producing a signal upon exposure to a transportable molecule which is transportable by the first component, the components comprising a carrier moiety or set of carrier moieties, the carrier moiety or set of carrier moieties comprising a receptor or transporter, the carrier or carrier set comprising one or more of: a cell, a liposome, an organelle, a protein, and a protein-lipid complex.

18. The method of claim 1, wherein the third component is a modulator that enhances or inhibits the transporter activity of the first component.

19. The method of claim 18, the method further comprising flowing the third component into contact with the first component in the first channel prior to introduction of the second component and the transporter molecule.

* * * * *